(12) United States Patent
Mallard et al.

(10) Patent No.: US 10,857,080 B2
(45) Date of Patent: *Dec. 8, 2020

(54) LIPID MICROCAPSULES PREFERABLY COMPRISING A LIPOPHILIC ACTIVE SUBSTANCE AND COMPOSITION CONTAINING SAME, METHOD FOR THE PRODUCTION THEREOF, AND USE OF SAME IN DERMATOLOGY AND IN COSMETICS

(71) Applicant: GALDERMA RESEARCH & DEVELOPMENT, Biot (FR)

(72) Inventors: Claire Mallard, Mougins (FR); Carole Dubayle, Mouans-Sartoux (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 15 days.

This patent is subject to a terminal disclaimer.

(21) Appl. No.: 15/101,331

(22) PCT Filed: Dec. 4, 2014

(86) PCT No.: PCT/EP2014/076659
§ 371 (c)(1),
(2) Date: Jun. 2, 2016

(87) PCT Pub. No.: WO2015/082660
PCT Pub. Date: Jun. 11, 2015

(65) Prior Publication Data
US 2016/0303005 A1 Oct. 20, 2016

(30) Foreign Application Priority Data

Dec. 4, 2013 (FR) ..................... 13 62117

(51) Int. Cl.
*A61K 8/11* (2006.01)
*A61K 47/14* (2017.01)
(Continued)

(52) U.S. Cl.
CPC .................. *A61K 8/11* (2013.01); *A61K 8/37* (2013.01); *A61K 8/375* (2013.01); *A61K 8/553* (2013.01);
(Continued)

(58) Field of Classification Search
CPC .......... A61K 8/11; A61K 47/14; A61K 47/24; A61K 9/107; A61K 8/553; A61K 9/06; A61K 47/00; A61K 2800/412
See application file for complete search history.

(56) References Cited

U.S. PATENT DOCUMENTS

| | | | | |
|---|---|---|---|---|
| 5,100,591 A | * | 3/1992 | Leclef | A61K 9/1617 264/4.1 |
| 5,227,165 A | * | 7/1993 | Domb | A01N 25/26 264/4.1 |

(Continued)

FOREIGN PATENT DOCUMENTS

| | | |
|---|---|---|
| FR | 2805761 A1 | 9/2001 |
| WO | 91/07171 A1 | 5/1991 |

(Continued)

OTHER PUBLICATIONS

English Translation of the International Search Report dated Jan. 13, 2015 corresponding to International Patent Application No. PCT/EP2014/076659, 4 pages.

(Continued)

*Primary Examiner* — Lakshmi S Channavajjala
(74) *Attorney, Agent, or Firm* — Foley & Lardner LLP; Sunit Talapatra

(57) ABSTRACT

Lipid microcapsules are described that can include at least one lipophilic active substance, more specifically a retinoid, (Continued)

Figure 1:
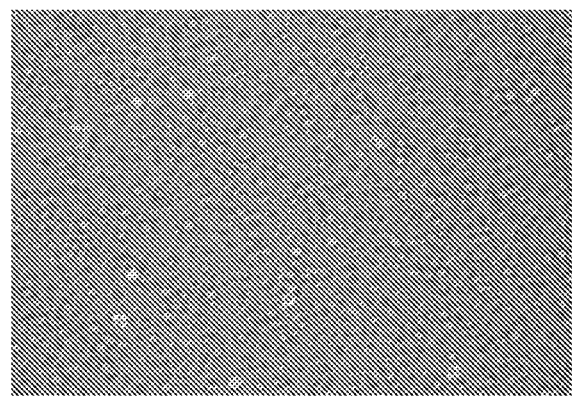

in a soluble form. Also described, are pharmaceutical compositions including the same and a method for the production thereof. Methods of using such a composition to treat dermatological pathologies are also described.

32 Claims, 3 Drawing Sheets

(51) Int. Cl.
| | |
|---|---|
| A61K 47/24 | (2006.01) |
| A61K 9/00 | (2006.01) |
| A61K 9/06 | (2006.01) |
| A61K 31/402 | (2006.01) |
| A61Q 19/00 | (2006.01) |
| A61K 31/192 | (2006.01) |
| A61K 8/37 | (2006.01) |
| A61K 31/203 | (2006.01) |
| A61K 8/67 | (2006.01) |
| A61K 8/86 | (2006.01) |
| A61K 31/216 | (2006.01) |
| A61K 9/50 | (2006.01) |
| A61K 8/55 | (2006.01) |
| A61K 9/107 | (2006.01) |
| A61K 31/05 | (2006.01) |
| A61K 31/12 | (2006.01) |
| A61K 31/5575 | (2006.01) |
| A61K 31/573 | (2006.01) |
| A61K 9/08 | (2006.01) |
| A61K 47/10 | (2017.01) |

(52) U.S. Cl.
CPC ............... *A61K 8/671* (2013.01); *A61K 8/86* (2013.01); *A61K 9/0014* (2013.01); *A61K 9/06* (2013.01); *A61K 9/08* (2013.01); *A61K 9/107* (2013.01); *A61K 9/5015* (2013.01); *A61K 31/05* (2013.01); *A61K 31/12* (2013.01); *A61K 31/192* (2013.01); *A61K 31/203* (2013.01); *A61K 31/216* (2013.01); *A61K 31/402* (2013.01); *A61K 31/5575* (2013.01); *A61K 31/573* (2013.01); *A61K 47/10* (2013.01); *A61K 47/14* (2013.01); *A61K 47/24* (2013.01); *A61Q 19/00* (2013.01); *A61K 2800/412* (2013.01)

(56) References Cited

U.S. PATENT DOCUMENTS

| | | | |
|---|---|---|---|
| 6,017,549 | A | 1/2000 | Knight et al. |
| 7,781,489 | B2 | 8/2010 | Menegatti et al. |
| 7,807,708 | B2 | 10/2010 | Biadatti et al. |
| 8,057,823 | B2 | 11/2011 | Heurtault et al. |
| 8,110,284 | B2 * | 2/2012 | Naigertsik ............. A01N 25/28 |
| | | | 428/321.1 |
| 8,309,121 | B2 * | 11/2012 | Baudonnet ........... A61K 9/0014 |
| | | | 424/452 |
| 2005/0048088 | A1 | 3/2005 | Zulli et al. |
| 2007/0134276 | A1 | 6/2007 | Menegatti et al. |
| 2007/0184076 | A1 | 8/2007 | Unger et al. |
| 2008/0167375 | A1 | 7/2008 | Weidner |
| 2008/0193393 | A1 | 8/2008 | Dayan |
| 2009/0258065 | A1 | 10/2009 | Baudonnet et al. |
| 2010/0098752 | A1 * | 4/2010 | Pinsky ..................... A61K 8/14 |
| | | | 514/1.1 |
| 2011/0195030 | A1 | 8/2011 | Mumper et al. |
| 2015/0125520 | A1 * | 5/2015 | Mallard ............... A61K 9/0014 |
| | | | 424/451 |
| 2016/0310439 | A1 * | 10/2016 | Mallard ............... A61K 9/0014 |

FOREIGN PATENT DOCUMENTS

| | | |
|---|---|---|
| WO | WO-95/03829 A1 | 2/1995 |
| WO | WO-2006/066978 A1 | 6/2006 |
| WO | WO-2010/072958 A2 | 7/2010 |
| WO | 2010/113111 A1 | 10/2010 |
| WO | 2011/036234 A1 | 3/2011 |
| WO | 2013/178749 A1 | 12/2013 |

OTHER PUBLICATIONS

International Search Report dated Jan. 13, 2015 corresponding to International Patent Application No. PCT/EP2014/076659, 5 pages.
Written Opinion of the International Searching Authority dated Jan. 13, 2015 corresponding to International Patent Application No. PCT/EP2014/076659, 7 pages.
Liu et al. "Isotretinoin-loaded solid lipid nanoparticles with skin targeting for topical delivery." International journal of pharmaceutics 328.2 (2007): 191-195.
U.S. Appl. No. 14/404,901, filed May 30, 2013.
U.S. Appl. No. 15/101,721, filed Dec. 4, 2014.
U.S. Appl. No. 15/577,857, filed Nov. 29, 2017.

* cited by examiner

LIPID MICROCAPSULES PREFERABLY COMPRISING A LIPOPHILIC ACTIVE SUBSTANCE AND COMPOSITION CONTAINING SAME, METHOD FOR THE PRODUCTION THEREOF, AND USE OF SAME IN DERMATOLOGY AND IN COSMETICS

CROSS-REFERENCE TO PRIOR APPLICATIONS

This application is a National Stage of PCT/EP2014/076659, filed Dec. 4, 2014, and designating the United States (published on Jun. 11, 2015, as WO 2015/082660 A1), which claims priority under 35 U.S.C. § 119 to French Patent Application No. 1362117, filed Dec. 4, 2013, each hereby expressly incorporated by reference in its entirety and each assigned to the assignee hereof.

The present invention relates to lipid microcapsules which have an oily internal phase and a non-polymeric shell obtained from at least one lipid compound chosen from amphiphilic lipids.

In particular, the invention relates to lipid microcapsules comprising at least one lipophilic active ingredient, said active agent being present in dissolved form in the oily core of the microcapsules.

The invention also relates to the primary emulsion composed of the microcapsules comprising an oily core, dispersed in an aqueous phase, and to the composition comprising the primary emulsion in an acceptable carrier.

The invention also relates to a method for preparing the primary emulsion, and the composition comprising the lipid microcapsules. Finally, the invention relates to a pharmaceutical composition for use thereof in the treatment of dermatological complaints.

Those skilled in the art are constantly confronted with difficulties in formulating active agents, in particular lipophilic active ingredients which have a pharmaceutical activity and/or a cosmetic activity, because of their solubility in a medium that can sometimes prove to be unfavorable. Moreover, once dissolved, the active agent has to be stable, as does the composition containing it.

The problem addressed here by the present invention is therefore that of designing a physically and chemically stable composition capable of facilitating the formulating of the active agent while at the same time improving the protection thereof and also the stability thereof in the composition into which it is incorporated.

Thus, the applicant has discovered, surprisingly, that the use of specific lipid microcapsules which make it possible to modify the structure of the interface between the active agent-dissolving medium and the external phase has an impact on the achieved content of dissolved active agent and on the stability thereof in a composition. In the present invention, the active agent is dissolved in the oily core of lipid microcapsules.

There are in the prior art many encapsulation techniques which make it possible to obtain microcapsules.

The term "microencapsulation" defines all of the technologies which make it possible to obtain the preparation of individualized microparticles, consisting of a coating material containing an active material.

The terminology "microcapsules" implies entities of which the diameter is between 1 and 1000 μm. The term "nanocapsules" is reserved for capsules of which the size is less than 1 micron.

The substance encapsulated may be in the form of fine particles of divided solid, of a liquid, or of a gaseous compound. The microcapsule makes it possible to preserve the encapsulated substance in the form of a finely divided state, and to release it under the desired conditions.

The microparticles obtained by microencapsulation may be in two types of distinct morphologies:

microspheres which are particles consisting of a continuous macromolecular or lipid network forming a matrix in which the active material is finely dispersed. The latter may be in the form of solid fine particles or else of droplets of solution;

microcapsules which are reservoir particles consisting of a core of liquid or solid active material, surrounded by a continuous solid shell of coating material.

The various microencapsulation methods can be categorized according to various criteria. Richard and Benoit, (Microencapsulation, 2000, Techniques de l'Ingénieur, J2210, 1-20) propose four different ways to categorize encapsulation methods:

the methods can be categorized according to whether or not organic solvent is used, some techniques, such as complex coacervation, using supercritical fluids, the nature of the dispersing medium can also be used as a basis for a categorization: it may be liquid (interfacial polycondensation, coacervation), gaseous (spray drying, fluidized bed coating), or in the supercritical state (phase separation), the family to which the compound used to obtain the capsule belongs may also make it possible to categorize the encapsulation modes: it is possible to use preformed polymers (coacervation), lipids (spray-congealing), or else monomers (interfacial polycondensation, polymerization in a dispersed medium), finally, a last categorization is based on the nature of the active ingredient according to which the microencapsulation is carried out: physicochemical methods are distinguished from chemical and mechanical methods.

The various encapsulation methods are summarized in the table presented below according to the nature of the method (Finch and Bodmeier, 2005, Microencapsulation, Wiley-VCH verlag GmbH & Co, KGa, Weinheim10.1002/14356007.a16_575).

| Type of method | Encapsulation mode | Microparticle size range | Type of products obtained |
|---|---|---|---|
| Physicochemical methods | Phase separation or coacervation (simple or complex) | 2-1200 μm | Microcapsules |
| | Evaporation - solvent extraction | 0.5-200 μm | Microcapsules Microspheres |
| | Melting of the encapsulation material (hotmelt) | | Microspheres |
| | Thermal gelling of emulsion | | Microspheres |

| Type of method | Encapsulation mode | Microparticle size range | Type of products obtained |
|---|---|---|---|
| Chemical methods | Interfacial polycondensation/polymerization<br>Radical or anionic polymerization in a dispersed medium | 2-2000 μm | Microcapsules<br>Microspheres<br>Microspheres |
| Mechanical methods | Spray drying/atomization | 1-200 μm | Microspheres |
| | Gelling or freezing of drops (prilling) | 200-800 μm | Microspheres |
| | Fluidized air bed coating (spray-coating) | 35-5000 μm | Microspheres |
| | Extrusion/spheronization | 200 μm | Microspheres |

Since the mechanical methods make it possible to obtain only microspheres, microcapsules are generally obtained by means of physicochemical or chemical methods. These methods require the use of preformed coating agents such as polymers or monomers which, in situ via a specific polymerization mechanism, allow the formation of the coating material.

In accordance with the present invention as defined hereinafter, the microcapsules and methods which make it possible to obtain them have the advantage, compared with the prior art, of not containing any polymer or any volatile organic solvent and of not involving temperature cycles.

According to the invention, the term "volatile solvent" is intended to mean any solvent considered to be unstable, i.e. having a boiling point strictly below 100° C. By analogy, any solvent having a boiling point above or equal to 100° C. will be considered nonvolatile according to the invention.

In the case of the majority of applications of microencapsulation, the active substances are firstly held and protected in the core of the microcapsules for a defined period of time, and secondly are either gradually released through the membrane according to a certain release rate, or released in bulk in one go. In this case, the release is triggered by a process ensuring a specific release.

The problem addressed here by the present invention is therefore that of designing a physically and chemically stable composition capable of containing at least one lipophilic active ingredient, for the treatment of dermatological pathological conditions, said active ingredient being in dissolved form. The composition according to the invention has in particular the objective of improving the formulating of the active ingredient while at the same time guaranteeing its stability and also easy use and a cosmeticity which is acceptable for application to all the areas of the body that may be affected by the pathological condition.

According to the invention, the term "physical stability" is intended to mean a composition of which the physical properties such as the organoleptic properties, the microcapsule size, the pH and the viscosity are stable over time and under various temperature conditions: 4° C., ambient temperature, 40° C.

According to the invention, the term "chemical stability" is intended to mean a composition capable of containing an active ingredient which is chemically stable over time regardless of the temperature condition: 4° C., ambient temperature, 40° C.

The term "ambient temperature" is intended to mean a temperature between 15 and 25° C.

According to the present invention, the lipophilic active ingredient is in a form that is dissolved in a stable composition.

Many lipophilic active agents often exhibit difficulties in terms of dissolution and stability, thus limiting the incorporation thereof into the carriers conventionally used, and making it difficult to obtain a stable composition.

Moreover, the addition of dissolving agent to topical formulations often increases the irritant capacity of the formulae, while at the same time inducing instability of the composition, and does not therefore provide an ideal solution to the problem encountered.

The composition according to the invention is thus capable of containing, in the microcapsules, at least one active ingredient known to those skilled in the art as having difficulties in terms of dissolution and stability. The active agents that can be used according to the invention may be, in a nonlimiting manner:

active agents with low solubility and low stability in a strongly aqueous medium, such as plant extracts, and in particular Indigo Naturalis. Other active agents that can preferentially be used according to the invention are also prostaglandin analogs. "Prostaglandin analogs" that may be mentioned include, in a nonlimiting manner, travoprost, latanoprost and tafluprost. Travoprost is preferably used;

active agents which exhibit pH-dependent degradation of the composition, such as corticoids, and in particular clobetasol and esters thereof, betamethasone and esters thereof, aclomethasome and esters thereof, which destabilize at pH>5. Preferably, clobetasol propionate is used;

oxidation-sensitive active agents, such as phenolic derivatives. "Phenolic derivatives" that may be mentioned include, in a nonlimiting manner, hydroquinone, rucinol or lucinol, resorcinol, 4-hydroxyanisole, hydroquinone monoethyl ether and hydroquinone monobenzoyl ether. Hydroquinone or rucinol is preferably used.

The term "lipid microcapsules" is intended to mean a vesicular system of micrometric size, i.e. of size greater than one micrometre, consisting of a non-polymeric lipid shell surrounding an oily core that is liquid or semiliquid at ambient temperature.

The term "oily core" or "lipid internal phase" is intended to mean the internal phase of the lipid microcapsules of micrometric size containing a water-immiscible lipophilic solvent.

The present invention therefore relates to the formulation of lipid microcapsules of micrometric size which can improve the formulating and the stability of lipophilic active ingredients, in the treatment of pathological skin complaints.

The oily core of the lipid microcapsules of micrometric size of the present invention is lipophilic, allowing the dissolution of hydrophobic active ingredients in larger amount.

The present invention is a system for using lipid microcapsules of micrometric size without the use of a volatile organic solvent often used for the formation of the shell, thus limiting the risks of toxicity and intolerance and in particular of irritation.

According to the present invention, the composition comprises lipid microcapsules of micrometric size and not lipid microspheres. In contrast, lipid microspheres are matrix particles, i.e. particles of which all of the mass is solid at ambient temperature. When microspheres contain a pharmaceutically acceptable active ingredient, it is finely dispersed or dissolved in the solid matrix. The lipid microcapsules of micrometric size according to the invention are particles of which the core is composed of one or more fatty substance(s) that is (are) liquid or semiliquid at ambient temperature and is capable of containing the active ingredient in dissolved form, and the shell of which is lipid and non-polymeric in nature. Indeed, the lipid microcapsules of micrometric size according to the invention require no polymer and therefore no in situ polymerization.

The Applicant has thus discovered, surprisingly, that compositions comprising at least one lipophilic active ingredient, in dissolved form in lipid microcapsules of micrometric size in a hydrophilic environment, not requiring the use of polymer or of volatile organic solvent, ensure the stability of the active agent by virtue of the encapsulation of said active ingredient in microcapsules. The compositions according to the invention may also promote the cutaneous penetration of the active agent, which is useful in the treatment of skin complaints.

A first subject of the present invention is therefore a lipid microcapsule of micrometric size containing an oily internal phase and a non-polymeric shell obtained from at least one lipid compound chosen from amphiphilic lipids.

Preferably, the lipid microcapsule of micrometric size according to the invention contains at least one lipophilic active ingredient dissolved in the oily internal phase.

In particular, the lipid microcapsules of micrometric size according to the invention preferably consist of:
  a non-polymeric shell obtained from at least one lipid compound;
  at least one oily core in which the lipophilic active agent is dissolved;
  at least one lipophilic active ingredient dissolved in said oily core.

The invention relates in particular to lipid microcapsules of micrometric size produced without volatile organic solvent.

A subject of the present invention is also a primary emulsion composed of lipid microcapsules of micrometric size dispersed in an aqueous phase.

The term "primary emulsion" is thus intended to mean the lipid system composed of the lipid microcapsules of micrometric size with a solid or semisolid interface, which are dispersed in a continuous aqueous phase, said microcapsules containing an oily core capable of containing the lipophilic active ingredient in dissolved form, and a shell obtained from a lipid compound, forming the semisolid or solid interface between the oily internal phase and the continuous aqueous phase. This primary emulsion is therefore an oil-in-water emulsion.

Said oil-in-water primary emulsion according to the invention can be incorporated in a pharmaceutically acceptable carrier, such as a gel, a solution or an emulsion, for instance a cream or a lotion.

The present invention therefore also relates to a composition comprising the primary emulsion according to the invention.

In particular, the present invention thus also relates to a composition, in particular a pharmaceutical and/or cosmetic composition, said composition comprising, in a pharmaceutically or cosmetically acceptable carrier, the primary emulsion according to the invention.

The present invention thus relates to a pharmaceutical composition, said composition comprising, in a pharmaceutically acceptable carrier, the primary emulsion composed of lipid microcapsules of micrometric size preferably consisting of:
  a non-polymeric shell obtained from at least one lipid compound;
  at least one oily core in which the lipophilic active ingredient is dissolved;
  at least one lipophilic active ingredient,
said lipid microcapsules of micrometric size being dispersed in an aqueous phase.

According to the invention, the term "composition" is thus intended to mean the primary emulsion, incorporated in a pharmaceutically acceptable carrier, such as an excipient or a mixture of excipients that can form a composition in the form of a gel, a solution or an emulsion, for instance a cream or a sprayable or non-sprayable lotion.

The compositions according to the invention have the advantage of being chemically and physically stable.

According to the present invention, the term "lipid microcapsules of micrometric size" is intended to mean lipid microsystems of which the size is preferentially between 1 µm and 100 µm.

According to one preferred production mode, 50% of the lipid microcapsules have at least one mean size of between 1 and 80 µm and preferentially of between 1 and 50 µm. In one particularly preferred mode, the microcapsules according to the invention have a mean size of between 1 and 20 µm.

The lipid microcapsules of micrometric size are present in the composition according to the invention in an amount of between 0.1% and 30%, preferably between 0.5% and 20% and more particularly between 1% and 10% by weight relative to the total weight of the composition.

The microcapsules each consist of a core that is liquid or semiliquid at ambient temperature and of a shell obtained from at least one lipid compound.

Preferably, the lipid microcapsules consist of a core that is liquid or semiliquid at ambient temperature, containing at least one lipophilic active ingredient dissolved in the oily core.

The prior art (U.S. Pat. No. 8,057,823, FR 2 805 761 and WO2011/036234) presents lipid capsules containing phosphatidylcholines, but said capsules are of nanometric size and, in order for them to be produced, require the systematic presence of at least one hydrophilic nonionic co-surfactant which is an oxyethylenated derivative of fatty alcohols and of fatty acids.

In contrast with the prior art, the present invention relates to lipid microcapsules of micrometric size containing exclusively phosphatidylcholines without any other additional lipophilic or hydrophilic co-surfactant.

The shell encapsulating the oily core that is liquid or semiliquid at ambient temperature is preferably composed of a non-polymeric material that is rigid at ambient temperature and the transition temperature or melting point of which is high. In order to be rigid at ambient temperature, the transition temperature or melting point must be greater than 35° C., preferably greater than 40° C. and ideally greater than 45° C.

In the microcapsules according to the invention, the shell consists of at least one lipophilic compound of amphiphilic type. Preferentially, the shell consists of only one lipid compound; advantageously chosen from amphiphilic lipids. More preferentially, the lipid compound is chosen from the family of phospholipids, and more specifically phosphatidylcholines or lecithins. Phosphatidylcholines or lecithins show good compatibility with the skin and have a very low irritant potential.

As lecithins that may be used, mention may be made in particular of natural or synthetic or derived soybean or egg lecithins. The first type of lecithin is phosphatidylcholine (PC). Other types of lecithin exist, including phosphatidylglycerol, phosphatidylinositol, sphingomyelin and phosphatidylethanolamine.

Among the lecithins with a transition temperature of greater than 35° C., mention may be made more particularly of dipalmitoylphosphatidylcholine (DPPC), distearoylphosphatidylcholine (DSPC), dibehenylphosphatidylcholine (DBPC), palmitoylstearoylphosphatidylcholine (PSPC), palmitoylbehenylphosphatidylcholine (PSPC) and stearoylbehenylphosphatidylcholine (SBPC), and also any saturated lecithins with long chains of fatty acids and derivatives thereof.

The lecithins in particular used in the present invention are solid at ambient temperature, which promotes the formation of a semisolid interface around the liquid or semiliquid core. This formulation allows the encapsulation of the active ingredient dissolved in the oily core.

The lipid microcapsules of micrometric size according to the invention more particularly contain a semisolid or solid interface between the internal phase and the aqueous continuous phase, by virtue of the use, as sole lipid compound, of a preferentially hydrogenated lecithin. More particularly, the hydrogenated lecithin used according to the invention has a high percentage of saturated phosphatidylcholine.

The term "high percentage" is intended to mean an amount of greater than 85% of hydrogenated (or saturated) phosphatidylcholine relative to the total weight of lecithin.

As lecithins preferentially used according to the invention, mention may be made of certain hydrogenated lecithins with a content of hydrogenated phosphatidylcholine of greater than 85%, for instance Lipoid® of grade P100-3, Phospholipon® of grade 90H sold by the company Lipoid, Epikuron® of grade 200 SH sold by Cargill, or Emulmetik® 950 sold by Lucas Meyer. Preferentially, the lecithin used as sole lipid compound is Phospholipon® 90H, for which the content of hydrogenated phosphatidylcholine is greater than 90% and the transition temperature of which is about 54° C.

The lipid compound surrounding the liquid or semiliquid core as defined above is present in an amount of between 0.01% and 10% by weight, preferably between 0.05% and 5% by weight and more preferentially between 0.1% and 1% by weight relative to the total weight of the composition.

The lipid compound, in particular the hydrogenated lecithin, according to the invention enables by itself the encapsulation of the active agent, which avoids contact of this active agent with the aqueous phase, and thus ensures its chemical stability. In particular, the lipid microcapsule, and in particular the shell, is free of any co-surfactant, in particular of lipophilic or hydrophilic co-surfactant.

The lipid microcapsules of micrometric size are in particular free of volatile organic solvent.

In particular, the lipid microcapsules of micrometric size are free of polymer.

For the purposes of the present invention, the term "active agent" is intended to mean a compound having a pharmaceutical activity and/or a cosmetic activity.

For the purposes of the present invention, the term "lipophilic" is intended to mean a compound that is soluble in a fatty substance that is liquid or semiliquid at ambient temperature or in a temperature range of between 25 and 90° C. In other words, a lipophilic substance is liposoluble.

Preferably, the lipophilic active ingredient is chosen from plant extracts, prostaglandin analogs, corticoids and phenolic derivatives.

According to one embodiment, the active ingredient is chosen from plant extracts, in particular Indigo Naturalis.

According to one embodiment, the active ingredient is chosen from prostaglandin analogs, in particular travoprost, latanoprost and tafluprost and more preferentially travoprost.

According to one embodiment, the active ingredient is chosen from corticoids, in particular clobetasol propionate.

According to one embodiment, the active ingredient is chosen from phenolic derivatives, preferentially hydroquinone, rucinol or lucinol, resorcinol, 4-hydroxyanisole, hydroquinone monoethyl ether and hydroquinone monobenzoyl ether. More preferentially, in accordance with this embodiment, the active ingredient is chosen from hydroquinone and rucinol.

Preferably, the active ingredient is chosen from Indigo Naturalis, travoprost, clobetasol propionate, hydroquinone and rucinol.

According to one embodiment, the lipophilic active ingredient has a cosmetic activity and can in particular be chosen from moisturising active agents and sunscreens.

The lipophilic active ingredient present in the microcapsules according to the present invention is different than an irritant active ingredient.

The composition according to the invention comprises between 0.001% and 10% of at least one lipophilic active ingredient, by weight relative to the total weight of the composition, preferably from 0.005% to 5% of an active agent, by weight relative to the total weight of the composition.

The lipophilic active ingredient is thus dissolved in the core of the lipid microcapsules of micrometric size according to the invention. Said core, or oily internal phase, comprises at least one fatty substance that is liquid or semiliquid at ambient temperature.

The composition of the internal phase is thus essential for the stability of the active ingredient. The oily internal phase must, of course, be capable of being compatible with the active agent to be dissolved, and be able to dissolve the active agent.

The term "phase that can dissolve the active agent" is intended to mean a phase in which the active ingredient is stable and has a solubility which allows it to be used at the active concentration in the final composition.

For the purposes of the invention, the term "stability of the active ingredient in the oily phase" is intended to mean that the active ingredient is chemically stable over time regardless of the temperature condition: 4° C., ambient temperature, 40° C.

The stability of the active ingredient in the oily phase is in particular evaluated by liquid chromatography coupled to a UV detector (HPLC-UV).

For the purposes of the present invention, the term "fatty substance that is liquid or semiliquid at ambient temperature" is intended to mean an oily solvent.

The term "oily solvent" is intended to mean any material that is water-immiscible at ambient temperature.

More particularly, the oily solvent may be a vegetable, mineral, animal or synthetic oil.

Among the vegetable oils, mention may be made, in a nonlimiting manner, of olive oil, almond oil, palm oil, soybean oil, sesame oil, canola oil, cottonseed oil, corn oil, safflower oil, castor oil or sunflower oil.

Among the mineral oils, mention may be made, in a nonlimiting manner, of liquid paraffins of various viscosities, for instance those sold by Exxon Mobil, Marcol 152®, Marcol 82® and Primol 352®.

Among the oils of animal origin, mention may be made, in a nonlimiting manner, of lanolin, squalene, cod liver oil, and squalane sold by the company Laserson under the trade name Cosbiol®.

Among the synthetic oils, mention may be made, in a nonlimiting manner, of triglycerides, fatty acid esters, fatty alcohols, polyethylene glycol ethers, the corresponding fatty alcohols and esters, polyethylene glycol ethers, amides or glycols.

In one preferred mode according to the invention, the oily solvent constituting the oily internal phase does not comprise any fatty acids which are not esterified or polyethoxylated.

More particularly, the oily solvent may be a mineral oil, a triglyceride, a fatty acid ester, a carboxylic acid ester, a fatty alcohol, a volatile or nonvolatile silicone, or a polyethylene glycol ether.

Among the mineral oils, mention may be made, in a nonlimiting manner, of liquid paraffin.

Among the triglycerides and oils containing the same, mention may be made, in a nonlimiting manner, of octanoic acid triglycerides or caprylic/capric acid triglycerides, such as those sold by the company Stearineries Dubois or those sold under the names Miglyol® 810, 812 and 818 by the company Sasol.

Among the fatty acid esters, mention may be made, in a nonlimiting manner, of the diisopropyl adipate such as the commercial product Crodamol® DA sold by the company Croda or Schercemol DIA Ester® sold by the company Lubrizol, or cetearyl isononanoate sold under the name Cetiol SN® by the company BASF.

Among the carboxylic acid esters, mention may be made, in a nonlimiting manner, of ($C_{12-15}$) alkyl benzoate, such as the commercial product Crodamol® AB sold by the company Croda, or propylene glycol caprylate sold under the name Capryol 90® by the company Gattefossé.

Among the fatty alcohols, mention may be made in a nonlimiting manner of octyldodecanol or octyldodecanol octanoate.

Among the polyethylene glycol ethers, mention may be made in a nonlimiting manner of the PPG-15 stearyl ether sold under the name Arlamol PS11E-LQ by the company Croda.

Among the volatile and nonvolatile silicones, mention may be made of dimethicones and cyclomethicones, such as those resold by Dow Corning under the trade name Q7-9120 silicone Fluid® and ST-Cyclomethicone 5-NF®.

In one preferred mode according to the invention, the solvents used in the oily internal phase are ($C_{12-15}$) alkyl benzoate, propylene glycol caprylate or caprylic/capric acid triglycerides.

In another preferred mode according to the invention, in the presence of an active ingredient, the preferred oily internal phase which is a solvent of the active ingredient is diisopropyl adipate or PPG-15 stearyl ether.

More particularly, the oily solvent may be a vegetable oil, a triglyceride, a fatty acid ester, a fatty alcohol or polyethylene glycol ethers.

In one preferred mode according to the invention, the oily solvent constituting the oily internal phase does not comprise any fatty acids which are not esterified or polyethoxylated.

In particular, those skilled in the art will choose the suitable oily solvent(s) according to the lipophilic active agent liable to be dissolved.

According to one preferred embodiment, the oily solvents that are preferred for dissolving Indigo Naturalis are olive oil or caprylic/capric acid triglycerides.

According to one preferred embodiment, the oily solvent that is preferred for dissolving travoprost is PPG-15 stearyl ether.

According to one preferred embodiment, the oily solvents that are preferred for dissolving clobetasol propionate are apricot kernel PEG-6 esters, PPG-15 stearyl ether or caprylic/capric acid triglycerides.

According to one preferred embodiment, the oily solvents that are preferred for dissolving hydroquinone are diisopropyl adipate or PPG-15 stearyl ether.

According to one preferred embodiment, the oily solvents that are preferred for dissolving rucinol are diisopropyl adipate, PPG-15 stearyl ether or caprylic/capric acid triglycerides.

According to one embodiment, the lipid microcapsules contain:
- an oily internal phase comprising at least one fatty substance that is liquid or semiliquid at ambient temperature, chosen from a vegetable oil, a triglyceride, a fatty acid ester, a fatty alcohol, or polyethylene glycol ethers,
- a non-polymeric shell obtained from at least one lipid compound,
- at least one active ingredient chosen from Indigo Naturalis, travoprost, clobetasol propionate, hydroquinone and rucinol, said active ingredient being dissolved in the oily internal phase.

Likewise, the oily internal phase may also contain one or more non-oily co-solvents or other co-solvents of nonvolatile organic type.

In one preferred mode according to the invention, the internal phase requires no solvents/co-solvent of alcoholic type in order to dissolve the active ingredient. The mixtures of solvents chosen according to the invention are sufficient to obtain the required solubility and stability of the active agent in the microcapsules without having recourse to any alcoholic solvent.

In addition to this or these oily solvent(s), the internal phase may also comprise one or more fatty substances that are liquid or semiliquid at ambient temperature and that cannot dissolve the active agent.

The term "fatty substance that cannot dissolve the active agent" is intended to mean a compound for which the active ingredient does not have a solubility which allows it to be used at the active concentration in the final composition.

In the oily internal phase, the solvent will be present in an amount of between 50% and 99.997% by weight relative to the total weight of the internal phase; preferably in an amount of between 70% and 99.997% and preferably between 95% and 99.997% by weight relative to the total weight of the internal phase.

In the oily internal phase, the optional co-solvent or fatty substance is present in an amount of between 0% and 50% by weight relative to the total weight of the internal phase; preferably in an amount of between 0.1% and 25% and preferably between 0.5% and 10% by weight relative to the total weight of the internal phase.

In addition to this or these oily solvent(s) and this or these fatty substance(s) which cannot dissolve the active agent, the internal phase may also comprise one or more compounds such as, for example, antioxidants or preservatives.

In the primary emulsion according to the invention, the oily internal phase of the microcapsules is present in an amount of between 0.1% and 50% by weight relative to the total weight of the primary emulsion, preferably in an amount of between 0.5% and 35% by weight relative to the total weight of the primary emulsion.

In the primary emulsion according to the invention, the ratio between the internal oily phase and the amount of hydrogenated lecithin is between 5 and 10 to 1.

Preferably, this ratio in the emulsion is between 6 and 8 to 1 and preferentially 7 to 1.

Moreover, the ratio between the water and the internal oily phase is between 1.25 and 5 to 1. Preferably, this ratio between the water and the internal oily phase is between 2 and 4 to 1 and preferentially 2 and 3 to 1.

In the primary emulsion, the microcapsules are dispersed in an aqueous phase. The continuous aqueous phase comprises water. This water may be demineralized water, a floral water, or a natural spring or mineral water.

The water may be present in a content of between 55% and 95% by weight relative to the total weight of the composition, preferably of between 60% and 95% by weight.

A subject of the present invention is thus a composition, in particular a pharmaceutical or cosmetic composition, said composition comprising the primary emulsion containing the lipid microcapsules of micrometric size defined above in the text of the present invention in a pharmaceutically or cosmetically acceptable carrier, such as a gel, a solution or an emulsion, for instance a cream or a lotion.

When the pharmaceutically or cosmetically acceptable carrier is a gel, the primary emulsion is dispersed in an aqueous phase which comprises at least one gelling agent.

This gelling agent may be a cellulose-based derivative chosen from semisynthetic cellulose-based gelling agents.

The gelling agent may also be chosen from natural gums, in particular xanthan gum (known for example under the name Satiaxane and sold by the company Cargill), starch and derivatives thereof, crosslinked polyacrylic acid polymers, for instance, carbomers, such as Carbopol 980 or Carbopol Ultrez 10 and from alkyl derivatives thereof, for instance copolymers of acrylates/C10-30 alkyl acrylate, such as Carbopol ETD2020, Pemulen TR1, Pemulen TR2, carboxyvinyl polymers, polyvinylpyrrolidones and derivatives thereof, and polyvinyl alcohols.

The gelling agent may also be chosen from emulsified polymers such as Sepigel 305 consisting of a polyacrylamide/C13-C14 isoparaffin/laureth-7 mixture, or Simulgel® 600PHA or Sepineo P600, namely sodium acryloyldimethyltaurate copolymer/isohexadecane/polysorbate 80. These two products are sold by the company SEPPIC.

When the pharmaceutically or cosmetically acceptable carrier is a solution, the primary emulsion is dispersed in a carrier composed of an aqueous phase.

The term "aqueous phase which constitutes the pharmaceutically acceptable carrier" is intended to mean any aqueous phase as defined previously in the present invention.

When the pharmaceutically or cosmetically acceptable carrier is a cream or a lotion, the primary emulsion is dispersed in a carrier composed of an aqueous phase and of a fatty phase optionally comprising at least one surfactant or emulsifier.

In the case of pharmaceutical or cosmetic carriers in cream or lotion form, the composition according to the invention thus comprises a fatty phase. This fatty phase may comprise, for example, vegetable oils, mineral oils, animal oils, synthetic oils or silicone oils, and mixtures thereof.

Preferably, when the carrier of the composition according to the invention is a cream or lotion, the emulsion is in the form of an oil-in-water (O1W) emulsion. This emulsion may or may not comprise at least one emulsifier.

The cream or lotion according to the invention also comprises an aqueous phase.

The term "aqueous phase which constitutes the pharmaceutically or cosmetically acceptable carrier, alone or in an emulsion" is intended to mean any aqueous phase as defined previously in the present invention.

The composition according to the invention may also contain, in the primary emulsion or the pharmaceutically acceptable carrier, one or more additives or combinations of additives, such as:

preservatives;
pro-penetrants;
stabilizers;
humectants;
humidity regulators;
pH regulators;
osmotic pressure modifiers;
chelating agents;
UV-A and UV-B screening agents;
and antioxidants.

Needless to say, those skilled in the art will take care to select the ingredients of the pharmaceutically or cosmetically acceptable carrier and in particular the aqueous phases, the fatty phases, the emulsifiers and also the optional compound(s) to be added to these compositions such that the advantageous properties intrinsically associated with the present invention are not, or are not substantially, adversely affected by the choice of the ingredients.

The composition according to the invention thus comprises, in a pharmaceutically or cosmetically acceptable carrier, on a weight basis relative to the total weight of the composition, microcapsules composed of:

a) a non-polymeric shell obtained from 0.01% to 10% of lipid compound chosen from amphiphilic lipids;
b) an oily core composed of from 0.1% to 50% of fatty substance that is liquid or semiliquid at ambient temperature;
c) 0.001% and 10% of at least one lipophilic active agent.

The composition according to the invention thus preferably comprises, in a pharmaceutically or cosmetically acceptable carrier, on a weight basis relative to the total weight of the composition, microcapsules composed of:

a) 0.1% to 5% of lipid compound chosen from amphiphilic lipids, preferably hydrogenated lecithin;
b) 1% to 30% of fatty substance that is liquid or semiliquid at ambient temperature, preferably fatty acid esters or polyethylene glycol ethers;
c) between 0.005% and 5% of at least one lipophilic active ingredient.

In a preferred embodiment according to the invention, the composition comprises, in a pharmaceutically acceptable carrier, on a weight basis relative to the total weight of the composition:

a) 0.1% to 5% of hydrogenated lecithin with a hydrogenated phosphatidylcholine content of greater than 85%;

b) 1% to 30% of fatty acid esters or of polyethylene glycol ethers;

c) 0.001% to 5% of at least one lipophilic active ingredient.

Preferably, the carrier is pharmaceutically acceptable.

The pharmaceutical composition that may be used according to the invention is intended for treating the skin and may be administered topically, parenterally or orally.

Via the oral route, the pharmaceutical composition may be in liquid or pasty form, and more particularly in the form of gel capsules, coated tablets or syrups.

Via the parenteral route, the composition may be in the form of suspensions for perfusion or for injection.

Preferably, the composition is in a form suitable for topical administration. The term "topical application" is intended to mean application to the skin, the mucous membranes, the hair or the scalp.

Via the topical route, the composition may be in liquid or pasty form, and more particularly in the form of creams, milks, pomades, impregnated pads, syndets, wipes, gels, sprays, foams, lotions, sticks, shampoos or washing bases.

A subject of the invention is also a process for preparing the compositions according to the invention. Preferably, a subject of the invention is the process for preparing the compositions comprising at least one lipophilic active agent.

The process according to the invention does not involve phase inversion phenomena characterized by a phase inversion temperature (PIT) (used in particular in patents FR 2 805 761 and FR 2 840 531), and therefore does not require temperature increase and decrease cycles.

The process according to the invention does not use a high pressure homogenizer (HPH) and does not therefore require a pre-homogenization step.

The process according to the invention therefore has the advantage of at the same time not having successive heating and cooling cycles, not using volatile organic solvent and polymer, and not requiring an emulsion gelling step or a pre-homogenization step.

The process as presented according to the invention and proposed for producing the lipid microcapsules of micrometric size uses equipment which allows high-shear emulsification.

Various devices can be used, for instance high-shear rotor/stator mixers, such as a Polytron (Kinematica) or the Magic Lab (Ika). In a manner likewise alternative to the rotor/stator, sonication may be used with, for example, a Branson probe. Whatever the type of equiment used, the process consists in producing a primary emulsion, which is then diluted in a pharmaceutically acceptable carrier.

This primary emulsion makes it possible to vary the mode of introduction of the lipid compound, preferably of the hydrogenated lecithin, which can be totally introduced into the oily phase (100% oily phase) or into the aqueous phase (100% aqueous phase) or introduced in various ratios, for instance a 50/50 ratio, into the oily phase and into the aqueous phase.

1—Preparation of the Primary Emulsion:

The production of the primary emulsion comprises 3 steps:
Preparation of the aqueous phase
Preparation of the oily phase
Mixing of the aqueous and oily phases.

The preparation of the aqueous phase and the preparation of the oily phase are dependent on the choice of the mode of dispersion of the lipid compound, preferably of the hydrogenated lecithin:

100% in aqueous phase or
100% in oily phase or
50/50% aqueous phase/oily phase.

a) Preparation of the primary emulsion with 100% dispersion of the lipid compound, preferably of the hydrogenated lecithin, in the aqueous phase:

Preparation of the Aqueous Phase:

In a container suitable for containing all of the primary emulsion, the hydrogenated lecithin used is dispersed in all of the aqueous phase heated to approximately 75° C., using a high shear rotor/stator type mixer such as an Ultra Turrax (Ika), a Polytron (Kinematica) or the Magic Lab (Ika), with stirring between 5000 and 10 000 rpm, for a defined period of time which will not exceed 30 minutes. A preservative and an antioxidant may be added to this phase.

Preparation of the Oily Phase:

The active ingredient, if present, is dissolved in the internal oily phase heated to approximately 75° C., comprising, inter alia, the oil for dissolving the active ingredient, in a suitable container and using a magnetic bar. A preservative and an antioxidant may be added to this phase after the active ingredient has been dissolved.

b) Preparation of the primary emulsion with 100% dispersion of the lipid compound, preferably of the hydrogenated lecithin, in the oily phase:

Preparation of the Aqueous Phase:

All of the aqueous phase is heated to 75° C. in a container suitable for containing all of the primary emulsion. A preservative and an antioxidant may be added to this phase.

Preparation of the Oily Phase:

The active ingredient, if present, is dissolved in the internal oily phase heated to approximately 75° C., comprising, inter alia, the oil for dissolving the active ingredient, in a suitable container and using a magnetic bar. A preservative and an antioxidant may be added to this phase after the active ingredient has been dissolved. The lipid compound, preferably the hydrogenated lecithin, used is dispersed in this oily phase still at approximately 75° C., using a high shear rotor/stator type mixer such as an Ultra Turrax (Ika) or a Polytron (Kinematica), with stirring between 5000 and 10 000 rpm, for a defined period of time which will not exceed 30 minutes.

c) Preparation of the primary emulsion with 50% of the hydrogenated lecithin dispersed in the aqueous phase and 50% in the oily phase:

Preparation of the Aqueous Phase:

In a container suitable for containing all of the primary emulsion, all of the aqueous phase is heated to 75° C. Approximately half the lipid compound, preferably the hydrogenated lecithin, used is dispersed in this aqueous phase still heated to approximately 75° C., using a high shear rotor/stator type mixer such as an Ultra Turrax (Ika), a Polytron (Kinematica) or the Magic Lab (Ika), with stirring between 5000 and 10 000 rpm, for a defined period of time which will not exceed 30 minutes. A preservative and an antioxidant may be added to this phase.

Preparation of the Oily Phase:

The active ingredient, if present, is dissolved in the internal oily phase heated to approximately 75° C., comprising, inter alia, the oil for dissolving the active ingredient, in a suitable container and using a magnetic bar. The other portion of the lipid compound, preferably of the hydrogenated lecithin, is dispersed in this oily phase still heated to approximately 75° C., using a high shear rotor/stator type mixer such as an Ultra Turrax (Ika) or a Polytron (Kinematica), with stirring between 5000 and 10 000 rpm, for a defined period of time which will not exceed 30 minutes. A preservative and an antioxidant may be added to this phase after the active ingredient has been dissolved.

Once the aqueous and oily phases have been prepared, they are mixed by incorporation of the oily phase into the aqueous phase. The procedure is dependent on the type of apparatus used. Three types of apparatus are preferentially used for mixing the two phases resulting in the primary emulsion according to the invention: the process with a Polytron, the process with a Magic Lab and the process with a sonication probe. According to the various types of stirrers, the emulsion is produced as described:

Process with a Polytron with temperature regulation at 75° C.:
Incorporation of the oily phase onto the aqueous phase gently, with stirring between 5000 and 10 000 rpm.
Once the incorporation has been achieved, stirring at a higher speed for a minimum of 30 minutes.

Process with a Magic Lab with temperature regulation at 75° C.:
Simultaneous incorporation of the aqueous phase and of the oily phase in the apparatus with stirring at a speed of less than 16 000 rpm if the lipid compound, preferably hydrogenated lecithin, was 100% dispersed in the fatty phase.
Incorporation of the oily phase onto the aqueous phase already present in the apparatus with stirring at a speed of less than 16 000 rpm if the lipid compound, preferably hydrogenated lecithin, was 100% dispersed in the aqueous phase.
Once the incorporation has been achieved, allow the mixture to circulate until it returns to ambient temperature.

Process with the sonication probe with temperature regulation fixed below 50° C.:
Incorporation of the oily phase onto the aqueous phase rapidly, at an ultrasound amplitude fixed at 80 microns,
leave the mixture under these conditions for several tens of seconds.

2—Preparation of the Final Composition According to the Invention

The primary emulsion previously obtained is then introduced into a previously prepared pharmaceutically acceptable carrier, of solution, cream, lotion or gel type.

In the case of a gel containing mainly only water and a gelling agent, the gelling step is carried out instantaneously at the end of the production of the primary emulsion:
Remove a predetermined amount of primary emulsion and
Incorporate it gently into a previously prepared gel, with gentle stirring. The stirring can be generated using a deflocculating paddle attached to a stirring motor of IKA or Rayneri type. Gentle stirring corresponds to a speed which makes it possible to obtain a homogenous gel after 20 min without generating excessive aeration of the formulation, for example a speed around 200 rpm.

Alternatively, to prepare a composition of gel type according to the invention, an amount of primary emulsion may be removed and then diluted in one part of water. This mixture is then thickened by adding a gelling agent.

The process for preparing the compositions according to the invention comprises the following steps:
(i) preparation of the primary emulsion by:
(a) dissolution of the active ingredient if present in a fatty substance that is liquid or semiliquid at ambient temperature, to obtain the oily phase;
(b) preparation of the aqueous phase;
(c) dispersion of the lipid compound in the oily phase obtained in (a) or in the aqueous phase obtained in (b) or partly in each of the oily and aqueous phases;
(d) heating of the two oily and aqueous phases separately to about 75° C.;
(e) mixing with stirring of the oily and aqueous phases obtained at the end of step (d);
(ii) incorporation of the composition obtained in the preceding step into a pharmaceutically acceptable carrier.

The applicant has discovered, surprisingly, that the mode of introduction of the lipid compound, and more particularly of the hydrogenated lecithin, is capable of having an influence on the stability over time of the microcapsules dispersed in the pharmaceutically acceptable carrier.

In accordance with the present invention, the microcapsules and processes making it possible to obtain them, as described above, have the advantage compared with the prior art of using alternative processes to the processes that use temperature increase and decrease cycles or high-pressure homogenizers.

Preferably, the lipid compound is introduced either 100% into the oily phase, or 100% into the aqueous phase, depending on the nature of the oily core chosen in order to dissolve therein the lipophilic active ingredient within the microcapsule.

More preferentially, the hydrogenated lecithin is introduced either 100% into the oily phase, or 100% into the aqueous phase, depending on the nature of the oily core chosen in order to dissolve therein the lipophilic active ingredient within the microcapsule.

In one preferred mode according to the invention, the preferred apparatus is the Magic Lab.

In one preferred mode according to the invention, the preferred mode of dispersion of the lipid compound, and more preferentially of the hydrogenated lecithin, is 100% in the fatty phase, in the case of the use of oily solvents of acid ester and triglyceride type, for instance diisopropyl adipate.

In another preferred mode according to the invention, the preferred mode of dispersion of the lipid compound, and more preferentially of the hydrogenated lecithin, is 100% in the aqueous phase, in particular in the case of the use of oily solvents of polyethylene glycol ether type, for instance PPG-15 stearyl ether.

In particular, those skilled in the art will choose the suitable oily solvent(s) according to the lipophilic active ingredient to be dissolved when the latter is present and thus the mode of dispersion of the lipid compound, and more preferentially of the hydrogenated lecithin.

In one of the preferred modes, the process for preparing a composition according to the invention comprises the following steps:
(i) preparation of the primary emulsion by:
a) dissolution of the active ingredient if present in the internal oily phase or oily core and dispersion of the lipid compound, and more preferentially of the hydrogenated lecithin, in this same oily phase heated to 75° C.;
b) preparation of the aqueous phase, heated to 75° C.;
c) simultaneous incorporation of the aqueous phase and of the oily phase in the apparatus with stirring at a speed of less than 16 000 rpm;
d) once the incorporation has been achieved, allow the mixture to circulate until it returns to ambient temperature;
(ii) incorporation of the primary emulsion into the pharmaceutically acceptable carrier.

In one of the preferred modes, the process for preparing a composition according to the invention comprises the following steps:

(i) preparation of the primary emulsion by:
  a) dissolution of the active ingredient if present in the internal oily phase or oily core heated to 75° C.;
  b) dispersion of the lipid compound, and more preferentially of the hydrogenated lecithin, in the aqueous phase, heated to 75° C.;
  c) incorporation of the oily phase onto the aqueous phase already present in the apparatus with stirring at a speed of less than 16 000 rpm;
  d) once the incorporation has been achieved, allow the mixture to circulate until it returns to ambient temperature;
(ii) incorporation of the primary emulsion into the pharmaceutically acceptable carrier.

Preferably, these preparation processes are carried out in the absence of volatile organic solvent.

As previously indicated, the composition according to the invention comprises, in a pharmaceutically or cosmetically acceptable carrier, lipid microcapsules of micrometric size dispersed in an aqueous phase, said lipid microcapsules of micrometric size containing an oily internal phase in which at least one lipophilic active ingredient is dissolved, and a non-polymeric shell obtained from at least one lipid compound chosen from amphiphilic lipids.

The composition according to the invention may be used as a medicament.

In particular, a subject of the invention is also the composition as previously defined, for use thereof for treating dermatological complaints, in particular human complaints, as defined below:

1) dermatological complaints associated with a keratinization disorder relating to cell differentiation and proliferation, in particular for treating common acne, comedonal acne, polymorphic acne, acne rosacea, nodulocystic acne, acne conglobata, senile acne, secondary acne such as solar acne, acne medicamentosa or occupational acne;

2) keratinization disorders, in particular ichthyosis, ichthyosiform conditions, lamellar ichthyosis, Darier's disease, palmoplantar keratoderma, leukoplakia, pityriasis rubra pilaris and leukoplakiform conditions, cutaneous or mucosal (buccal) lichen;

3) dermatological complaints with an inflammatory immuno-allergic component, with or without a cell proliferation disorder, and in particular all forms of psoriasis, whether cutaneous, mucosal or ungual, and even psoriatic arthritis, or else atopic dermatitis and the various forms of eczema;

4) skin disorders caused by exposure to UV radiation, and also for repairing or combating skin aging, whether it is photo-induced or chronological, or for reducing actinic keratoses and pigmentations, or any pathological conditions associated with chronological or actinic aging, such as xerosis, pigmentations and wrinkles;

5) any condition associated with benign dermal or epidermal proliferations, whether or not they are of viral origin, such as common warts, flat warts, molluscum contagiosum and epidermodysplasia verruciformis, or oral or florid papillomatoses;

6) dermatological disorders such as immune dermatoses, for instance lupus erythematosus, bullous immune diseases and collagen diseases, such as scleroderma;

7) stigmata of epidermal and/or dermal atrophy induced by local or systemic corticosteroids, or any other form of cutaneous atrophy;

8) cicatrization disorders, or for preventing or repairing stretch marks, or else for promoting cicatrization;

9) in the treatment of any complaint of fungal origin at the cutaneous level, such as tinea pedis and tinea versicolor;

10) pigmentation disorders, such as hyperpigmentation, melasma, hypopigmentation or vitiligo;

11) cutaneous or mucosal cancerous or precancerous conditions, such as actinic keratoses, Bowen's disease, in-situ carcinomas, keratoacanthomas and skin cancers such as basal cell carcinoma (BCC), squamous cell carcinoma (SCC) and cutaneous lymphomas such as T lymphoma.

Preferentially, the invention relates to the composition for use thereof in the treatment of acne, ichthyosis, ichthyosiform conditions, palmoplantar hyperkeratosis or psoriasis.

In other words, the invention relates to the composition according to the invention for use thereof as a medicament in the treatment of dermatological complaints, in particular human complaints, as previously defined.

In particular, the invention relates to the use of the composition according to the invention for the treatment of dermatological complaints, in particular human complaints, as previously defined.

In particular, the composition is used for the treatment of acne, ichthyosis, ichthyosiform conditions, palmoplantar hyperkeratosis or psoriasis.

The composition according to the invention may be a cosmetic composition.

According to one embodiment, the cosmetic composition is used for cutaneous protection and/or care of the skin.

Preferentially, the cosmetic composition is used for caring for, in particular for moisturizing, the skin.

According to another embodiment, the cosmetic composition is used for protecting the skin against the effects of ultraviolet radiation.

Preferentially, the cosmetic composition is used for preventing or delaying the signs of skin aging due to ultraviolet radiation.

Various composition formulations comprising a lipophilic active agent will now be given, as illustrations and with no limiting nature.

EXAMPLE 1

Primary Emulsions Containing the Placebo Lipid Microcapsules Before Dilution in a Composition By using the preparation processes previously mentioned and according to the mode of dispersion of the hydrogenated lecithin as previously defined in the present description, lipid microcapsules were prepared with an oily core containing an oil or a mixture of oils.

The compositions of the primary emulsions E1 to E5 are therefore the following:

| | Compositions (% w/w) | | | | |
| --- | --- | --- | --- | --- | --- |
| Ingredients | E1 | E2 | E3 | E4 | E5 |
| Diisopropyl adipate | 27.89 | 27.89 | 27.89 | — | — |
| PPG-15 stearyl ether | — | — | — | 27.89 | — |
| Capric/caprylic acid triglycerides | — | — | — | — | 27.89 |
| Hydrogenated lecithin | 4.04 | 4.04 | 4.04 | 4.04 | 4.04 |
| Propyl paraben | 0.56 | 0.28 | 0.14 | 0.56 | 0.56 |
| Methyl paraben | 1.12 | 0.56 | 0.28 | 1.12 | 1.12 |
| Purified water | Qs 100 | Qs 100 | Qs 100 | Qs 100 | Qs 100 |

EXAMPLE 2

Examples of Compositions in the Form of a Gel According to the Invention Prepared from the Placebo Primary Emulsions of Compositions E1 to E5 of Example 1

In order to prepare the compositions in gel form G1 to G16 according to the invention various amounts of primary emulsions prepared according to example 1 were taken and diluted in a gel base.

To obtain a gel of 100 grams comprising approximately 5% of encapsulated oil, 17.784 grams of the placebo primary emulsion are added to the formulation. In the table below, the gels G1, G6, and G9 to G12 were obtained from the primary emulsion E1, the gels G4, G7, and G13 to G16 were obtained from the primary emulsion E4 and the gels G5 and G8 were obtained from the primary emulsion E5.

To obtain a gel of 100 grams comprising 10% of encapsulated oil, 35.855 grams of the primary emulsion E2 of example 1 are added to the formulation (the case of the gel G2).

To obtain a gel of 100 grams comprising 20% of encapsulated oil, 71.71 grams of the primary emulsion E3 of example 1 are added to the formulation (the case of the gel G3).

Examples of compositions in gel form obtained according to the invention are thus as follows:

Formulation of the Gels G1 to G8

| Ingredients | Compositions (% w/w) | | | | | | | |
| --- | --- | --- | --- | --- | --- | --- | --- | --- |
| | G1 | G2 | G3 | G4 | G5 | G6 | G7 | G8 |
| Diisopropyl adipate | 4.96 | 10 | 20 | — | — | 4.96 | — | — |
| PPG-15 stearyl ether | — | — | — | 4.96 | — | — | 4.96 | — |
| Capric/caprylic acid triglycerides | — | — | — | — | 4.96 | — | — | 4.96 |
| Hydrogenated lecithin | 0.72 | 1.4 | 2.90 | 0.72 | 0.72 | 0.72 | 0.72 | 0.72 |
| Methyl paraben | 0.2 | 0.2 | 0.2 | 0.2 | 0.2 | 0.2 | 0.2 | 0.2 |
| Propyl paraben | 0.1 | 0.1 | 0.1 | 0.1 | 0.1 | 0.1 | 0.1 | 0.1 |
| Sodium acryloyldimethyltaurate copolymer/ isohexadecane/ polysorbate 80 | 2 | 2 | 4 | 2 | 2 | 4 | 4 | 4 |
| Sodium docusate | — | — | — | — | — | 0.05 | 0.05 | 0.05 |
| Disodium edetate | — | — | — | — | — | 0.1 | 0.1 | 0.1 |
| Glycerol | — | — | — | — | — | 4.0 | 4.0 | 4.0 |
| Propylene glycol | — | — | — | — | — | 4 | 4 | 4 |
| Poloxamer P124 | — | — | — | — | — | 0.2 | 0.2 | 0.2 |
| Lactic acid (qs pH 3.5-4) | — | — | — | — | — | Qs pH | Qs pH | Qs pH |
| Purified water | Qs 100 | Qs 100 | Qs 100 | Qs 100 | Qs 100 | Qs 100 | Qs 100 | Qs 100 |

Formulation of the Gels G9 to G16

| Ingredients | Compositions (% w/w) | | | | | | | |
| --- | --- | --- | --- | --- | --- | --- | --- | --- |
| | G9 | G10 | G11 | G12 | G13 | G14 | G15 | G16 |
| Diisopropyl adipate | 4.96 | 4.96 | 4.96 | 4.96 | — | — | — | — |
| PPG-15 stearyl ether | — | — | — | — | 4.96 | 4.96 | 4.96 | 4.96 |
| Hydrogenated lecithin | 0.72 | 0.72 | 0.72 | 0.72 | 0.72 | 0.72 | 0.72 | 0.72 |
| Methyl paraben | 0.2 | 0.2 | 0.2 | 0.2 | 0.2 | 0.2 | 0.2 | 0.2 |
| Propyl paraben | 0.1 | 0.1 | 0.1 | 0.1 | 0.1 | 0.1 | 0.1 | 0.1 |
| Sodium hydroxide (qs pH 4.5-5) | Qs pH | Qs pH | Qs pH | Qs pH | Qs pH | Qs pH | Qs pH | Qs pH |
| Carbomer | 0.5 | 0.7 | — | — | 0.5 | 0.7 | — | — |
| Crosslinked copolymer Acrylates/alkyl ($C_{10-30}$) Acrylate | — | — | 0.7 | 1 | — | — | 0.7 | 1 |
| Purified water | Qs 100 | Qs 100 | Qs 100 | Qs 100 | Qs 100 | Qs 100 | Qs 100 | Qs 100 |

EXAMPLE 3

Examples of Compositions in the Form of a Cream According to the Invention Prepared from the Placebo Primary Emulsions of Compositions E1, E4 and E5 of Example 1

In order to prepare compositions in cream form C1 to C3 according to the invention, an amount of primary emulsion prepared according to example 1 was taken and integrated at a predetermined moment during the process for preparing a cream.

To obtain a cream of 100 grams comprising approximately 5% of oil in the capsules, 17.784 grams of the primary emulsion are added to the formulation.

The primary emulsions E1, E4 and E5 produce respectively the creams C1, C2 and C3 described in the table below.

Examples of compositions in cream form obtained according to the invention are thus as follows:

|  | Compositions (% w/w) | | |
| --- | --- | --- | --- |
| Ingredients | C1 | C2 | C3 |
| Diisopropyl adipate | 4.96 | — | — |
| PPG-15 stearyl ether | — | 4.96 | — |
| Capric/caprylic acid triglycerides | — | — | 4.96 |
| Hydrogenated lecithin | 0.72 | 0.72 | 0.72 |
| Methyl paraben | 0.2 | 0.2 | 0.2 |
| Propyl paraben | 0.1 | 0.1 | 0.1 |
| Sodium acryloyldimethyltaurate copolymer/isohexadecane/polysorbate 80 | 4 | 4 | 4 |
| Sodium docusate | 0.05 | 0.05 | 0.05 |
| Disodium edetate | 0.1 | 0.1 | 0.1 |
| Glycerol | 2 | 2 | 2 |
| Propylene glycol | 3 | 3 | 3 |
| Poloxamer P124 | 0.1 | 0.1 | 0.1 |
| Allantoin | 0.2 | 0.2 | 0.2 |
| Talc | 2.0 | 2.0 | 2.0 |
| Xanthan gum | 0.5 | 0.5 | 0.5 |
| Lactic acid (qs pH 3.5-4) | Qs pH | Qs pH | Qs pH |
| Dimethicone | 1.0 | 1.0 | 1.0 |
| Cyclomethicone 5 | 8.0 | 8.0 | 8.0 |
| Liquid paraffin | 1.0 | 1.0 | 1.0 |
| Purified water | Qs 100 | Qs 100 | Qs 100 |

EXAMPLE 4

Characterization of the Compositions in Gel Form of Example 2 G1, G4 and G5 According to the Invention, Prepared from the Placebo Primary Emulsions E1, E4 and E5 that were Obtained According to Two Different Modes of Introduction of the Hydrogenated Lecithin Each test carried out is described below:
The macroscopic observation is performed on the formulation in its original packaging.
The microscopic observation is performed using an Axio-.Scope A1 microscope (polarized light, objective ×20).
The pH measurement is taken in the formulation.
The viscosity measurement is performed using an apparatus of Brookfield RVDVII+ type. The measurements are performed after 1 min, in the original packaging.

In the present examples, the primary emulsions E1, E4 and E5 of example 1 were prepared according to two distinct modes of introduction of the hydrogenated lecithin, namely 100% of the hydrogenated lecithin in the aqueous phase and 100% of the hydrogenated lecithin in the fatty phase.

Each primary emulsion therefore results in the production of two gels, called Gel No. 1 and Gel No. 2 in the table below.

The equipment used for preparing the primary emulsions is the Magic Lab.

It should be noted that:
Gels No. 1 and No. 2 obtained from the primary emulsion E1 have the same formulation as the gel G1 described in example 2,
Gels No. 1 and No. 2 obtained from the primary emulsion E4 have the same formulation as the gel G4 described in example 2,
Gels No. 1 and No. 2 obtained from the primary emulsion E4 have the same formulation as the gel G4 described in example 2,

|  |  | Hydrogenated lecithin dispersion mode | |
| --- | --- | --- | --- |
| Composition/Oil | Characterizations | 100% aqueous phase Gel No. 1 | 100% fatty phase Gel No. 2 |
| E1/Diisopropyl adipate | Macroscopic observation | White gel | White gel |
| | Microscopic observation | Capsules of micrometric size | Capsules of micrometric size |
| | pH | 4.37 | 5.41 |
| | Viscosity RV, S06, 10 rpm | 57 800 cP | 56 990 cP |
| E4/PPG-15 stearyl ether | Macroscopic observation | White gel | White gel |
| | Microscopic observation | Capsules of micrometric size | Capsules of micrometric size but sometimes misshapen |
| | pH | 5.34 | 5.39 |
| | Viscosity RV, S06, 10 rpm | 45 900 cP | 46 500 cP |
| E5/Capric/caprylic acid triglycerides | Macroscopic observation | White gel | White gel |
| | Microscopic observation | Capsules of micrometric size | Capsules of micrometric size |

-continued

|  |  | Hydrogenated lecithin dispersion mode | |
|---|---|---|---|
| Composition/Oil | Characterizations | 100% aqueous phase Gel No. 1 | 100% fatty phase Gel No. 2 |
|  | pH | 5.19 | 5.30 |
|  | Viscosity RV, S06, 10 rpm | 52 000 cP | 56 200 cP |

Depending on the oil used in the formulation, the hydrogenated lecithin dispersion mode can generate different characteristics.

Figure 2:
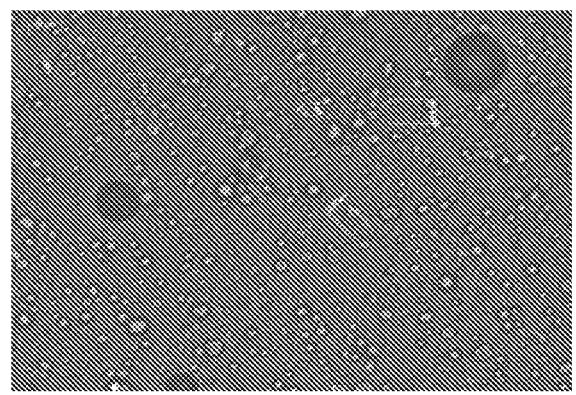

FIGS. 1 and 2 represent the images obtained under a microscope (objective 40 and magnification ×252) of the microcapsules in gels No. 1 and No. 2 respectively that were prepared from the primary emulsion E4 containing PPG-15 stearyl ether as oil.

The microscopic observation of the microcapsules reveals that the microcapsules in gels No. 1 and No. 2 differ in terms of polydispersity and shape.

Indeed, it is observed that the microcapsules of FIG. 1 are uniform in size and in shape. On the other hand, those of FIG. 2 are more non-uniform, both in terms of size and in terms of shape. Thus, for another defined oil, the hydrogenated lecithin dispersion mode can have an effect on the physical appearance of the microcapsules.

Figure 3:
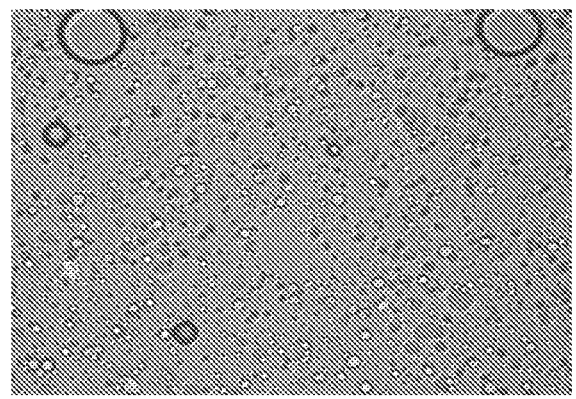
Figure 4:
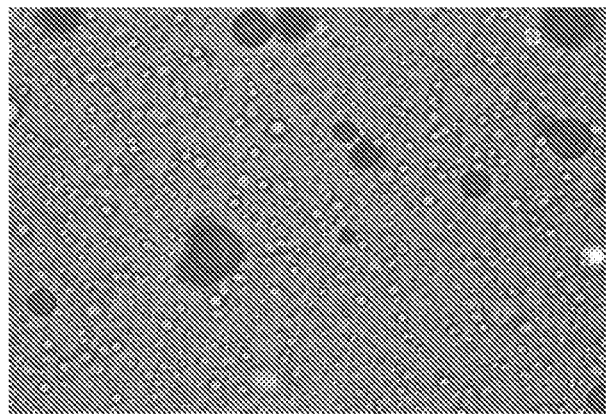

FIGS. 3 and 4 represent the images obtained under a microscope (objective 40 and magnification ×252) of the microcapsules in gels No. 1 and No. 2 respectively that were prepared from the primary emulsion E5 containing capric/caprylic acid triglycerides as oil.

The microscopic observation of the microcapsules reveals that the microcapsules in gels No. 1 and No. 2 do not differ in terms of polydispersity and shape.

Thus, for another defined oil, the hydrogenated lecithin dispersion mode does not have an effect on the physical appearance of the microcapsules.

The observations therefore demonstrate that the conditions which result in a better production of microcapsules can be dependent on the hydrogenated lecithin dispersion mode according to the oil used.

In this respect, a hydrogenated lecithin dispersion mode may be preferred for each oil type.

In one preferred mode according to the invention, with acid esters and triglycerides, for instance diisopropyl adipate, as oily solvent, the preferred hydrogenated lecithin dispersion mode is 100% in the fatty phase.

In one preferred mode according to the invention, with polyethylene glycol ethers, for instance PPG-15 stearyl ether, as oily solvent, the preferred hydrogenated lecithin dispersion mode is 100% in the aqueous phase.

EXAMPLE 5

Study of the Stability of Gels No. 1 and No. 2 of Example 4 According to the Oil Used (from the Emulsions E4 and E5 of Example 1) and According to the Hydrogenated Lecithin Introduction Mode The stability of gels No. 1 and No. 2, described in example 4 and obtained from the primary emulsion E4 of example 1, is studied over a period of 6 months at ambient temperature, at 4° C. and at 40° C.

Each test carried out is described below:

The macroscopic observation is performed on the formulation in its original packaging.

The microscopic observation is performed using an Axio-.Scope A1 microscope (polarized light, objective ×20).

The pH measurement is taken in the formulation.

The viscosity measurement is performed using an apparatus of Brookfield RVDVII+ type. The measurements are performed after 1 min, in the original packaging.

Gel No. 1: Dispersion in Aqueous Phase Obtained from the Primary Emulsion E4 of Example 1 (Oil Used: PPG-15 Stearyl Ether)

| Characterizations | Storage conditions | Stability at 6 months |
|---|---|---|
| Macroscopic appearance | T0 | White gel |
|  | AT | IDEM T0 |
|  | 4° C. | IDEM T0 |
|  | 40° C. | IDEM T0 |
| Microscopic appearance | T0 | Micrometric capsules |
|  | AT | Slight deformation of the capsules |
|  | 4° C. | Slight deformation of the capsules |
|  | 40° C. | Slight deformation of the capsules |
| pH Viscosity RV, S06, 10 rpm | T0 | pH = 5.34 45 900 cP |
|  | AT | pH = 5.67 46 100 cP |
|  | 40° C. | pH = 6.00 45 900 cP |
| Conclusions |  | Stable gel |

Gel No. 2: Dispersion in Fatty Phase Obtained from the Primary Emulsion E4 of Example 1 (Oil Used: PPG-15 Stearyl Ether)

| Characterizations | Storage conditions | Stability at 6 months |
|---|---|---|
| Macroscopic appearance | T0 | White gel |
|  | AT | IDEM T0 |
|  | 4° C. | IDEM T0 |
|  | 40° C. | IDEM T0 |
| Microscopic appearance | T0 | Micrometric capsules |
|  | AT | Considerable deformation of the capsules |
|  | 4° C. | Considerable deformation of the capsules |
|  | 40° C. | Considerable deformation of the capsules |

| Characterizations | Storage conditions | Stability at 6 months |
|---|---|---|
| pH | T0 | pH = 5.39 |
| Viscosity | | 46 500 cP |
| RV, S06, 10 rpm | AT | pH = 5.29 |
| | | 46 300 cP |
| | 40° C. | pH = 5.75 |
| | | 42 800 cP |
| Conclusions | | Gel with deformed microcapsules |

The stability of gels No. 1 and No. 2, described in example 4 and obtained from the primary emulsion E5 of example 1, is studied over a period of 6 months at ambient temperature, at 4° C. and at 40° C.

Gel No. 1: Dispersion in Aqueous Phase Obtained from the Emulsion E5 of Example 1 (Oil Used: Capric/Caprylic Acid Triglycerides)

| | Storage conditions | Stability at 6 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH | T0 | pH = 5.19 |
| Viscosity | | 52 000 cP |
| RV, S06, 10 rpm | AT | pH = 5.42 |
| | | 50 800 cP |
| | 40° C. | pH = 5.58 |
| | | 49 800 cP |
| Conclusions | | Stable gel |

Gel No. 2: Dispersion in Fatty Phase Obtained from the Composition E5 of Example 1 (Oil: Capric/Caprylic Acid Triglycerides)

| | Storage conditions | Stability at 6 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH | T0 | pH = 5.30 |
| Viscosity | | 56 2000 cP |
| RV, S06, 10 rpm | AT | pH = 5.41 |
| | | 55 800 cP |
| | 40° C. | pH = 5.51 |
| | | 47 600 cP |
| Conclusions | | Stable gel |

Figure 5:
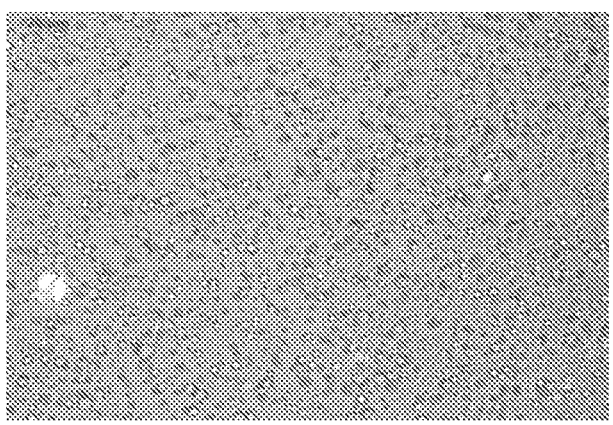
Figure 6:
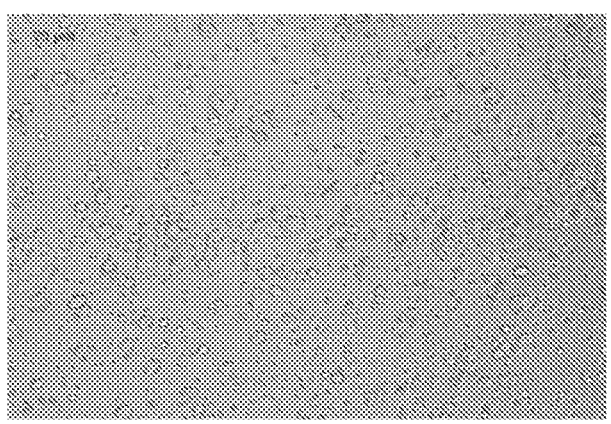

FIGS. 5 and 6 represent the images obtained under a microscope (objective 40 and magnification ×252) of the microcapsules in gels No. 1 and No. 2 that were prepared from the primary emulsion E4 containing PPG-15 stearyl ether as oil after 6 months of storage at a temperature of 40° C.

Microscopic observation of the microcapsules in gels No. 1 and No. 2 proves to be significant regarding the stability of the microcapsules according to the hydrogenated lecithin dispersion mode.

With 100% dispersion of the hydrogenated lecithin in the fatty phase, the microcapsules are very non-uniform in size and are deformed (FIG. 6).

With 100% dispersion of the hydrogenated lecithin in the aqueous phase, the microcapsules are more uniform and more even in size (FIG. 5).

The observations therefore demonstrate that the conditions which result in better stability of the capsules over time are 100% dispersion of the hydrogenated lecithin in the aqueous phase, in the case of the use of PPG-15 stearyl ether.

Figure 7:
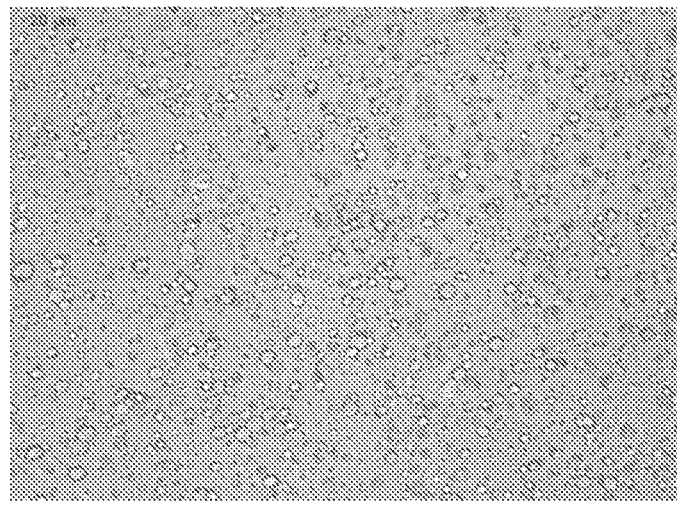
Figure 8:
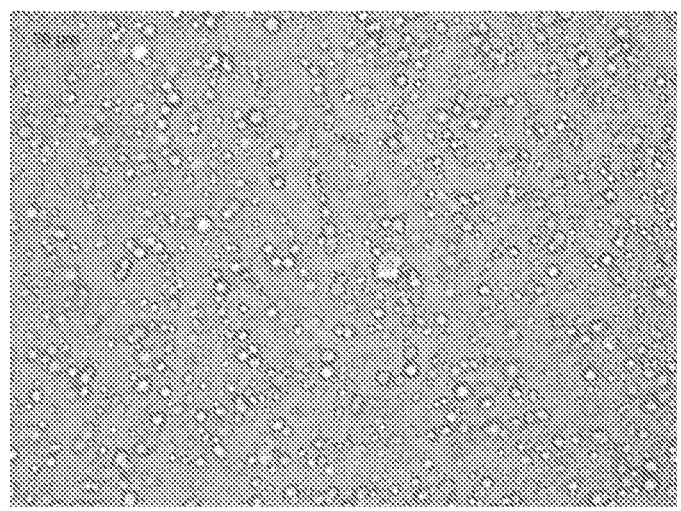

FIGS. 7 and 8 show the images obtained under a microscope of the microcapsules in gels No. 1 and No. 2 that were prepared from the primary emulsion E5 containing capric/caprylic acid triglycerides after 6 months of storage at a temperature of 40° C.

The microcapsules are as a whole uniform and even in size, after 6 months of stability at 40° C. (FIGS. 7 and 8).

The observations therefore demonstrate that the conditions which result in stability of the microcapsules over time can occur with a 100% dispersion of the hydrogenated lecithin in the aqueous phase or a 100% dispersion in the fatty phase, in the case of the use of capric/caprylic acid triglycerides.

In this respect and in the light of these results, a hydrogenated lecithin dispersion mode may be all the more justified for each oil type.

EXAMPLE 6

Characterization of Compositions in the Form of a Gel According to the Invention, Prepared from the Placebo Primary Emulsion E1 of Example 1

In the examples, the equipment that was used for preparing the primary emulsion is the Magic Lab.

The preferred dispersion mode for the hydrogenated lecithin with diisopropyl adipate is 100% in the fatty phase.

In the table below, gels No. 1, No. 2 and No. 3 have the same formulation as gels G1, G9 and G11 described in example 2.

| Primary emulsion/ Oil | Characterizations | Thickeners | | |
|---|---|---|---|---|
| | | sodium acryloyldimethyltaurate copolymer/isohexadecane/ polysorbate 80 Composition G1 Gel No. 1 | Carbomer Composition G9 Gel No. 2 | Crosslinked copolymer Acrylates/alkyl ($C_{10-30}$) Acrylate Composition G11 Gel No. 3 |
| E1/ Diisopropyl adipate | Macroscopic observation | White gel | White gel | White gel |
| | Microscopic observation | Capsules micrometric size | Capsules of micrometric size | Capsules of micrometric size |
| | pH | 5.12 | 4.87 | 5.03 |
| | Viscosity RV, S06, 10 rpm | 55 400 cP | 64 900 cP | 33 700 cP |

EXAMPLE 7

Study of Stability of the Gels of Example 6

Gel No. 1 (Thickener: Sodium Acryloyldimethyltaurate Copolymer/Isohexadecane/Polysorbate 80) Obtained from the Primary Emulsion E1 (Oil Used: Diisopropyl Adipate)

| Characterizations | Storage conditions | Stability at 3 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH | T0 | pH = 5.12 |
| Viscosity RV, S06, 10 rpm | | 55 400 cP |
| | AT | pH = 5.28 |
| | | 51 500 cP |
| | 40° C. | pH = 4.96 |
| | | 47 500 cP |
| Conclusions | | Stable gel |

Gel No. 2 (Thickener Used: Carbomer) Obtained from the Primary Emulsion E1 (Oil Used Diisopropyl Adipate)

| Characterizations | Storage conditions | Stability at 2 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH | T0 | pH = 4.87 |
| Viscosity RV, S06, 10 rpm | | 64 900 cP |
| | AT | pH = 4.93 |
| | | 61 800 cP |
| | 40° C. | pH = 4.84 |
| | | 55 200 cP |
| Conclusions | | Stable gel |

Gel No. 3 (Thickener: Acrylates/C10-30 Alkyl Acrylate Crosspolymer) Obtained from the Primary Emulsion E1 (Oil Used Diisopropyl Adipate)

| Characterizations | Storage conditions | Stability at 2 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH | T0 | pH = 5.03 |
| Viscosity RV, S06, 10 rpm | | 33 700 cP |
| | AT | pH = 5.08 |
| | | 38 000 cP |
| | 40° C. | pH = 4.89 |
| | | 40 800 cP |
| Conclusions | | Stable gel |

The results show that the gels obtained are stable at one month or at three months at ambient temperature or at a temperature of 40° C., whatever the nature of the thickener used.

EXAMPLE 8

Characterization of the Compositions in the Form of a Gel of Example 2 G2 and G3 According to the Invention, Prepared from Placebo Primary Emulsions E2 and E3 of Example 1

In the present examples, the equipment that was used for preparing the primary emulsions is the Magic Lab.

The primary emulsions E2 and E3 were prepared by introducing 100% of the hydrogenated lecithin into the fatty phase in order to obtain the corresponding gels.

It should be noted that gels No. 1 and No. 2 correspond to gels G2 and G3 of example 2.

| Oil | Characterizations | Primary emulsion E2 Gel No. 1 | Primary emulsion E3 Gel No. 2 |
|---|---|---|---|
| Diisopropyl adipate | Macroscopic observation | White gel | White gel |
| | Microscopic observation | Capsules of micrometric size | Capsules of micrometric size |
| | pH | 5.24 | 5.15 |
| | Viscosity | 47 300 Cp (RV, S06, 10 rpm) | 142 000 cP (RV, S07, 10 rpm) |

EXAMPLE 9

Study of Stability of the Gels of Example 8

The stability of the gels of example 8, obtained from the primary emulsions E2 and E3, was studied for a period of one month.

Gel No. 1 Obtained from the Primary Emulsion E2 of Example 1 (Oil Used: 10% of Diisopropyl Adipate)

| Characterizations | Storage conditions | Stability at 1 month |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH | T0 | pH = 5.24 |
| Viscosity | | 47 300 cP |
| RV, S06, 10 rpm | AT | pH = 5.21 |
| | | 45 700 cP |
| | 40° C. | pH = 5.16 |
| | | 43 600 cP |
| Conclusions | | Stable gel |

Gel No. 2 Obtained from the Primary Emulsion E3 of Example 1 (Oil Used: 20% of Diisopropyl Adipate)

| Characterizations | Storage conditions | Stability at 1 month |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH | T0 | pH = 5.15 |
| Viscosity | | 142 000 cP |
| RV, S07, 10 rpm | AT | pH = 4.83 |
| | | 118 000 cP |
| | 40° C. | pH = 5.13 |
| | | 102 000 cP |
| Conclusions | | Stable gel |

The results show that the gels obtained are stable for a period of one month at ambient temperature or a temperature of 40° C., whatever the content of diisopropyl adipate used, of the primary emulsion.

EXAMPLE 10

Primary Emulsions Containing the Lipid Microcapsules Containing a Lipophilic Active Agent Before Dilution in a Composition By using the processes previously mentioned and according to the hydrogenated lecithin dispersion mode as previously defined in the present description, lipid microcapsules were prepared and contain in the oily core a lipophilic active agent dissolved in an oil.

The lipophilic active agents used in the primary emulsions are Indigo Naturalis, travoprost, clobetasol propionate, hydroxy quinone and rucinol.

The compositions of the primary emulsions E'1 to E'11 are therefore the following:

| | Composition (% w/w) | | | | | |
|---|---|---|---|---|---|---|
| Ingredients | E'1 | E'2 | E'3 | E'4 | E'5 | E'6 |
| *Indigo Naturalis* | 0.014 | 0.014 | — | — | — | — |
| Travoprost | — | — | 0.007 | — | — | — |
| Clobetasol proprionate | — | — | — | 0.140 | 0.093 | 0.07 |
| Butyl Hydroxy Toluene | 0.139 | — | — | — | — | — |
| *Olea Europea* (olive) fruit oil | 27.89 | — | — | — | — | — |
| Capric/caprylic acid triglycerides | — | 27.89 | — | — | — | 27.89 |
| PPG-15 stearyl ether | — | — | 27.89 | — | 27.89 | — |
| Apricot kernel oil PEG-6 esters | — | — | — | 27.89 | — | — |
| Hydrogenated lecithin | 4.042 | 4.042 | 4.042 | 4.042 | 4.042 | 4.042 |
| Methyl paraben | 0.279 | 0.279 | 0.279 | 0.558 | 0.372 | 0.279 |
| Propyl paraben | 0.14 | 0.14 | 0.14 | 0.279 | 0.186 | 0.14 |
| Purified water | Qs 100 | Qs 100 | Qs 100 | Qs 100 | Qs 100 | Qs 100 |

| | Compositions (% w/w) | | | | |
|---|---|---|---|---|---|
| Ingredients | E'7 | E'8 | E'9 | E'10 | E'11 |
| Hydroquinone | 2.789 | 2.789 | — | — | — |
| Rucinol | — | — | 9.297 | 9.297 | 13.945 |
| Ascorbyl palmitate | 0.028 | 0.028 | 0.037 | 0.037 | 0.056 |
| Capric/caprylic acid triglycerides | — | — | 27.89 | — | — |
| Diisopropyl adipate | 27.89 | — | — | — | 27.89 |
| PPG-15 stearyl ether | — | 27.89 | — | 27.89 | — |
| Hydrogenated lecithin | 4.042 | 4.042 | 4.042 | 4.042 | 4.042 |
| Methyl paraben | 0.279 | 0.279 | 0.372 | 0.372 | 0.558 |
| Propyl paraben | 0.140 | 0.140 | 0.186 | 0.186 | 0.279 |
| Purified water | Qs 100 | Qs 100 | Qs 100 | Qs 100 | Qs 100 |

EXAMPLE 11

Examples of Compositions in the Form of a Gel According to the Invention Prepared from the Primary Emulsions E'1 to E'2 Containing Indigo Naturalis of Example 10

In order to prepare compositions in the form of a gel according to the invention, an amount of primary emulsion prepared according to example 11 was taken and added to the formulation.

To obtain a gel of 100 grams containing 0.01% of Indigo Naturalis, contained in the presence of 20% solvent oil in the microcapsules, 71.71 grams of the primary emulsion are added to the formulation.

Preferentially, 71.71 grams of the primary emulsion are added with stirring to 26.29 grams of water. This mixture is then thickened by adding a gelling agent at 2%, with moderate stirring.

The stirring can be generated using a deflocculating paddle attached to a stirring motor of IKA or Rayneri type. Moderate stirring corresponds to a speed which makes it possible to obtain a homogeneous gel after 20 minutes without generating excessive aeration of the formulation, for example a speed between 400-600 rpm.

In the table below, gels G'1 and G'2 were respectively obtained from the primary emulsions E'1 and E'2.

| Ingredients | Composition (% w/w) | |
| --- | --- | --- |
|  | G'1 | G'2 |
| Indigo Naturalis | 0.01 | 0.01 |
| Olea Europaea (olive) fruit oil | 20 | — |
| Capric/caprylic acid triglycerides | — | 20 |
| Butyl hydroxy Toluene | 0.1 | — |
| Hydrogenated lecithin | 2.90 | 2.90 |
| Methyl paraben | 0.2 | 0.2 |
| Propyl paraben | 0.1 | 0.1 |
| Sodium acryloyldimethyltaurate copolymer/ isohexadecane/polysorbate 80 | 2 | 2 |
| Purified water | Qs 100 | Qs 100 |

EXAMPLE 12

Examples of Compositions in the Form of a Gel According to the Invention, Prepared from the Primary Emulsion E'3 Containing Travoprost of Example 10

In order to prepare compositions in the form of a gel according to the invention, an amount of primary emulsion prepared according to example 11 was taken and added to the formulation.

To obtain a gel of 100 grams containing 0.005% of Travoprost, contained in the presence of 20% solvent oil in the microcapsules, 71.71 grams of the primary emulsion E'3 are added to the formulation.

Preferentially, 71.71 grams of the primary emulsion E'3 are added with stirring to 26.29 grams of water. This mixture is then thickened by adding a gelling agent at 2%, with moderate stirring.

The stirring can be generated using a deflocculating paddle attached to a stirring motor of IKA or Rayneri type. Moderate stirring corresponds to a speed which makes it possible to obtain a homogeneous gel after 20 min without generating excessive aeration of the formulation, for example a speed between 400-600 rpm.

In the table below, gel G'3 was obtained from the primary emulsion E'3.

| Ingredients | Composition (% w/w) G'3 |
| --- | --- |
| Travoprost | 0.005 |
| PPG-15 stearyl ether | 20 |
| Hydrogenated lecithin | 2.90 |
| Methyl paraben | 0.2 |
| Propyl paraben | 0.1 |
| Sodium acryloyldimethyltaurate copolymer/ isohexadecane/polysorbate 80 | 2 |
| Purified water | Qs 100 |

EXAMPLE 13

Examples of Compositions of Gel and Cream Type According to the Invention Prepared from the Primary Emulsions E'4 to E'6 of Example 10 Containing Clobetasol Propionate In order to prepare compositions of gel type according to the invention, an amount of primary emulsion prepared according to example 11 was taken and added to the formulation.

To obtain a gel of 100 grams containing 0.05% of clobetasol propionate, contained in the presence of 20% solvent oil in the capsules, 71.71 grams of the primary emulsion E'6 are added to the formulation.

Preferentially, 71.71 grams of the primary emulsion E'6 are added with stirring to 26.29 grams of water having a pH equal to 5. This mixture is then thickened by adding a gelling agent at 2%, with moderate stirring.

The stirring can be generated using a deflocculating paddle attached to a stirring motor of IKA or Rayneri type. Moderate stirring corresponds to a speed which makes it possible to obtain a homogeneous gel after 20 minutes without generating excessive aeration of the formulation, for example a speed between 400-600 rpm.

Likewise, to obtain a gel of 100 grams containing 0.05% of clobetasol propionate, contained in the presence of 15% solvent oil in the capsules, 53.78 grams of the primary emulsion are added to the formulation.

Preferentially, 53.78 grams of the primary emulsion E5 are added with stirring to 44.22 grams of water having a pH equal to 5. This mixture is then thickened by adding a gelling agent at 2%, with moderate stirring.

In the table below, gels G'4 and G'5 were respectively obtained from the primary emulsions E5 and E'6.

In order to prepare compositions in the form of a cream according to the invention, an amount of primary emulsion prepared according to the example was taken and added to the formulation.

To obtain a cream of 100 grams containing 0.05% of clobetasol propionate, contained in the presence of 10% solvent oil in the capsules, 35.855 grams of the primary emulsion E'4 are added to the formulation.

Preferentially, 35.855 grams of the primary emulsion are added with stirring to 57.145 grams of water having a pH equal to 5. This mixture is then thickened by adding a gelling agent at 4%, with moderate stirring.

After obtaining a smooth gel, 5 grams of cyclomethicone are incorporated into said gel with moderate stirring. A cream is thus obtained.

In the table below, the cream C'1 was obtained from the primary emulsion E'4.

| Ingredient | Composition (% w/w) | | |
|---|---|---|---|
| | C'1 | G'4 | G'5 |
| Clobetasol propionate | 0.05 | 0.05 | 0.05 |
| Apricot kernel oil PEG-6 esters | 10 | — | — |
| PPG-15 stearyl ether | — | 15 | — |
| Capric/caprylic acid triglycerides | — | — | 20 |
| Hydrogenated lecithin | 1.45 | 2.17 | 2.90 |
| Methyl paraben | 0.2 | 0.2 | 0.2 |
| Propyl paraben | 0.1 | 0.1 | 0.1 |
| Sodium acryloyldimethyltaurate copolymer/ isohexadecane/polysorbate 80 | 4 | 2 | 2 |
| Cyclomethicone | 5 | — | — |
| Citric acid | Qs pH 5 | Qs pH 5 | Qs pH 5 |
| Purified water | Qs 100 | Qs 100 | Qs 100 |

EXAMPLE 14

Examples of Compositions in the Form of a Gel According to the Invention Prepared from the Primary Emulsions E'7 to E'8 of Example 10 Containing Hydroquinone In order to prepare compositions of gel type according to the invention, an amount of primary emulsion prepared according to the example was taken and added to the formulation.

To obtain a gel of 100 grams containing 2% of hydroquinone, contained in the presence of 20% solvent oil in the microcapsules, 71.71 grams of the primary emulsion are added to the formulation.

Preferentially, 71.71 grams of the primary emulsion are added with stirring to 26.29 grams of water having a pH equal to 5. This mixture is then thickened by adding a gelling agent at 2%, with moderate stirring.

The stirring can be generated using a deflocculating paddle attached to a stirring motor of IKA or Rayneri type.

Moderate stirring corresponds to a speed which makes it possible to obtain a homogeneous gel after 20 minutes without generating excessive aeration of the formulation, for example a speed between 400-600 rpm.

In the table below, gels G'6 and G'7 were obtained from the primary emulsions E'7 and E'8.

| Ingredients | Composition (% w/w) | |
|---|---|---|
| | G'6 | G'7 |
| Hydroquinone | 2 | 2 |
| Ascorbyl palmitate | 0.02 | 0.02 |
| Diisopropyl adipate | 20 | — |
| PPG-15 stearyl ether | — | 20 |
| Hydrogenated lecithin | 2.90 | 2.90 |
| Methyl paraben | 0.2 | 0.2 |
| Propyl paraben | 0.1 | 0.1 |
| Sodium acryloyldimethyltaurate copolymer/ isohexadecane/polysorbate 80 | 2 | 2 |

-continued

| Ingredients | Composition (% w/w) | |
|---|---|---|
| | G'6 | G'7 |
| Citric acid | Qs pH 5 | Qs pH 5 |
| Purified water | Qs 100 | Qs 100 |

EXAMPLE 15

Examples of Compositions of Gel and Cream Type According to the Invention Prepared from the Primary Emulsions E'9 to E'11 of Example 10 Containing rucinol In order to prepare compositions of gel type according to the invention, an amount of primary emulsion prepared according to example 11 was taken and added to the formulation.

To obtain a gel of 100 grams containing 5% of rucinol, contained in the presence of 15% solvent oil in the capsules, 53.78 grams of the primary emulsion are added to the formulation.

Preferentially, 53.78 grams of the primary emulsion are added with stirring to 44.22 grams of water having a pH equal to 5. This mixture is then thickened by adding a gelling agent at 2%, with moderate stirring.

The stirring can be generated using a deflocculating paddle attached to a stirring motor of IKA or Rayneri type. Moderate stirring corresponds to a speed which makes it possible to obtain a homogeneous gel after 20 minutes without generating excessive aeration of the formulation, for example a speed between 400-600 rpm.

In the table below, gels G'8 and G'9 were respectively obtained from the primary emulsions E'10 and E'9.

In order to prepare compositions of cream type according to the invention, an amount of primary emulsion prepared according to example 11 was taken and added to the formulation.

To obtain a cream of 100 grams containing 5% of rucinol, contained in the presence of 10% solvent oil in the microcapsules, 35.855 grams of the primary emulsion E11 are added to the formulation.

Preferentially, 35.855 grams of the primary emulsion E11 are added with stirring to 57.145 grams of water having a pH equal to 5.

This mixture is then thickened by adding a gelling agent at 4%, with moderate stirring.

After obtaining a smooth gel, 5 grams of cyclomethicone are incorporated into said gel with moderate stirring. A cream is thus obtained.

In the table below, the cream C'2 was obtained from the primary emulsion E'11 of example 11.

| Ingredients | Composition (% w/w) | | |
|---|---|---|---|
| | C'2 | G'8 | G'9 |
| Rucinol | 5 | 5 | 5 |
| Ascorbyl palmitate | 0.02 | 0.02 | 0.02 |
| Diisopropyl adipate | 10 | — | — |
| PPG-15 stearyl ether | — | 15 | — |
| Capric/caprylic acid triglycerides | — | — | 15 |

-continued

| Ingredients | Composition (% w/w) | | |
|---|---|---|---|
| | C'2 | G'8 | G'9 |
| Hydrogenated lecithin | 1.45 | 2.17 | 2.17 |
| Methyl paraben | 0.2 | 0.2 | 0.2 |
| Propyl paraben | 0.1 | 0.1 | 0.1 |
| Sodium acryloyldimethyltaurate copolymer/isohexadecane/polysorbate 80 | 4 | 2 | 2 |
| Cyclomethicone | 5 | — | — |
| Citric acid | Qs pH 5 | Qs pH 5 | Qs pH 5 |
| Purified water | Qs 100 | Qs 100 | Qs 100 |

The invention claimed is:

1. A dermatological or cosmetic emulsion comprising a plurality of lipid microcapsules dispersed in an aqueous phase, wherein the lipid microcapsules comprise:
  (i) an oily internal phase comprising at least one fatty substance that is liquid or semiliquid at ambient temperature selected from the group consisting of polyethoxylated fatty acids, triglycerides, oils comprising the triglycerides, fatty acid esters, and polyethylene glycol ethers; and
  (ii) a non-polymeric shell obtained from at least one amphiphilic lipid compound comprising a hydrogenated lecithin with a weight amount of phosphatidylcholine of greater than 85%,
  wherein the lipid microcapsule has a mean size between 1 μm and 80 μm.

2. The emulsion as in claim 1, further comprising at least one lipophilic active ingredient dissolved in the oily internal phase.

3. The emulsion as in claim 1, wherein the lipid compound is present in an amount between 0.01% and 10% by weight relative to the total weight of the microcapsule.

4. The emulsion as claimed in claim 1, wherein the lipid compound has a transition temperature greater than 35° C.

5. The emulsion as claimed in claim 1, wherein the microcapsule is free of co-surfactant.

6. The emulsion as claimed in claim 1, wherein the microcapsule is free of volatile organic solvent.

7. The emulsion as claimed in claim 1, wherein the microcapsule is free of polymer.

8. The emulsion as in claim 1, wherein the at least one fatty substance comprises a fatty acid ester or polyethylene glycol ether.

9. The emulsion as in claim 1, wherein the at least one fatty substance comprises diisopropyl adipate or PPG-15 stearyl ether.

10. The emulsion as in claim 1, wherein the at least one fatty substance is present in an amount of between 50% and 99.997% by weight relative to the total weight of the oily internal phase.

11. The emulsion as in claim 2, wherein the lipophilic active ingredient is selected from the group consisting prostaglandin analogs, corticoids and phenolic derivatives.

12. The emulsion as in claim 2, wherein the lipophilic active ingredient is a plant extract is from Indigo Naturalis.

13. The emulsion as in claim 11, wherein the prostaglandin analogs are selected from the group consisting of travoprost, latanoprost and tafluprost.

14. The emulsion as in claim 11, wherein the corticoids are selected from the group consisting of clobetasol and esters thereof, betamethasone and esters thereof, and aclomethasome and esters thereof.

15. The emulsion as in claim 11, wherein the phenolic derivatives are selected from the group consisting of hydroquinone, rucinol or lucinol, resorcinol, 4-hydroxyanisole, hydroquinone monoethyl ether and hydroquinone monobenzoyl ether.

16. The emulsion as in claim 1, which is an oil-in-water type emulsion.

17. The emulsion as in claim 16, having a ratio of the internal oily phase to the amount of hydrogenated lecithin between 5:1 and 10:1, respectively.

18. The emulsion as in claim 16, having a ratio of water to the internal oily phase between 1.5:1 and 5:1, respectively.

19. A composition comprising the emulsion as in claim 1 and a pharmaceutically or cosmetically acceptable carrier.

20. The composition as in claim 19, wherein the pharmaceutically or cosmetically acceptable carrier is a gel.

21. The composition as in claim 19, wherein the pharmaceutically or cosmetically acceptable carrier is a solution.

22. The composition as in claim 19, wherein the pharmaceutically or cosmetically acceptable carrier is a cream.

23. The composition as in claim 19, wherein the composition comprises, in a pharmaceutically or cosmetically acceptable carrier, on a weight basis relative to the total weight of the composition, microcapsules comprised of:
  a) 0.01% to 10% of the amphiphilic lipid compound;
  b) 0.1% to 50% of the fatty substance that is liquid or semiliquid at ambient temperature; and
  c) 0.001% to 10% of at least one lipophilic active ingredient.

24. The composition as in claim 19, wherein the composition comprises, in a pharmaceutically or cosmetically acceptable carrier, on a weight basis relative to the total weight of the composition:
  a) 0.1% to 1% of a hydrogenated lecithin;
  b) 1% to 5% of a fatty acid ester or of polyethylene glycol ether; and
  c) 0.001% to 5% of at least one lipophilic active ingredient.

25. The composition as claimed in claim 19, wherein the composition is in a form suitable for topical administration.

26. The emulsion as in claim 1, wherein the lipid microcapsule has a mean size of between 1 μm and 50 μm.

27. The emulsion as in claim 1, wherein the lipid microcapsule has a mean size of between 1 μm and 20 μm.

28. The emulsion as in claim 3, wherein the lipid compound is present in an amount between 0.05% and 5% by weight relative to the total weight of the microcapsule.

29. The emulsion as in claim 3, wherein the lipid compound is present in an amount of between 0.1% and 1% by weight relative to the total weight of the microcapsule.

30. The emulsion as in claim 4, wherein the transition temperature is greater than 45° C.

31. The emulsion as in claim 13, wherein the prostaglandin analog is travoprost.

32. The emulsion as in claim 1, wherein the lipid microcapsule has a mean size between 20 μm and 80 μm.

* * * * *